US008735093B2

(12) United States Patent
Yokoyama et al.

(10) Patent No.: US 8,735,093 B2
(45) Date of Patent: May 27, 2014

(54) MUTANT PYRROLYSYL-TRNA SYNTHETASE, AND METHOD FOR PRODUCTION OF PROTEIN HAVING NON-NATURAL AMINO ACID INTEGRATED THEREIN BY USING THE SAME

(75) Inventors: Shigeyuki Yokoyama, Kanagawa (JP); Kensaku Sakamoto, Kanagawa (JP); Tatsuo Yanagisawa, Kanagawa (JP); Takatsugu Kobayashi, Kanagawa (JP)

(73) Assignee: Riken, Wako-Shi (JP)

( * ) Notice: Subject to any disclaimer, the term of this patent is extended or adjusted under 35 U.S.C. 154(b) by 0 days.

(21) Appl. No.: 12/727,037

(22) Filed: Mar. 18, 2010

(65) Prior Publication Data
US 2010/0267087 A1      Oct. 21, 2010

Related U.S. Application Data

(63) Continuation of application No. PCT/JP2008/067029, filed on Sep. 19, 2008.

(30) Foreign Application Priority Data

Sep. 20, 2007   (JP) ................. 2007-243574

(51) Int. Cl.
*C12P 21/00* (2006.01)
*C12N 9/00* (2006.01)
*C12N 15/52* (2006.01)
*C12N 15/63* (2006.01)

(52) U.S. Cl.
USPC ....... 435/69.1; 435/183; 435/320.1; 435/325; 435/252.3; 536/23.2

(58) Field of Classification Search
None
See application file for complete search history.

(56) References Cited

U.S. PATENT DOCUMENTS

| 2006/0166319 A1 | 7/2006 | Chan et al. |
| 2006/0183888 A1 | 8/2006 | Chan et al. |
| 2010/0304431 A1 | 12/2010 | Yokoyama et al. |

FOREIGN PATENT DOCUMENTS

| EP | 1911840 A1 | 4/2008 |
| JP | 2007-37445 A | 2/2007 |
| WO | WO-2004/070024 A1 | 8/2004 |
| WO | WO 2007/015527 A1 | 2/2007 |

OTHER PUBLICATIONS

Wang et al. Science Apr. 20, 2001: vol. 292 No. 5516 pp. 498-500.*
Kavran, J.M. et al., "Structure of pyrrolysyl-tRNA synthetase, an archeael enzyme for genetic code innovation", Proc. Natl. Acad. Sci USA, 2007, vol. 104, No. 27, pp. 11268-11273.
Zhang, Y., et al., "Crystal structures of apo wild-type *M. jannaschii* tyrosyl-tRNA synthetase (TyrRS) and an engineered TyrRS specific for O-methyl-L-tyrosine", Protein Science, 2005, vol. 14, pp. 1340-1349.
Polycarpo, C.R. et al., "Pyrrolysine analogues as substrates for pyrrolysyl-tRNA sythetase", FEBS Letters, 2006, vol. 580, pp. 6695-6700.
Mukai, T. et al., "Adding L-lysine derivatives to the genetic code of mammalian cells with engineered pyrrolysyl-tRNA sythetases", Biochem. Biophys. Res. Commun., 2008, vol. 371, pp. 818-822.
Kobayashi, T. et al., "In vivo site-specific introduction of non-natural main-chain/side-chain structures into proteins by using primitive aminoacyl-tRNA synthetases", Seikagaku, 2007, Shoroku CD, 4P-0337.
Yanagisawa, T. et al., "Crystallographic studies on multiple conformational states of active-site loops in pyrrolysyl-tRNA synthetase", J. Mol. Biol., 2008, vol. 378, pp. 634-652.
Yanagisawa, T. et al., "Site-specific incorporation of unnatural amino acids into protein by using pyrrolysyl-tRNA synthetase", RNA Meeting, 2006, vol. 8, pp. 1.
Yanagisawa, T. et al., "Crystallization and preliminary X-ray crystallographic anaysis of the catalytic domain of pyrrolysyl-tRNA synthetase from the methanogenic archaeon *Methanosarcina mazei*", Acta Crystallographica, 2006, vol. F62, pp. 1031-1033.
Sakamoto, Kensaku, et al., "Site-specific incorporation of an unnatural amino acid into proteins in mammalian cells", Nucleic Acids Research, 2002, vol. 30, pp. 4692-4699.
Tsao, M. et al., "Selective Staudinger Modification of Proteins Containing *p*-Azidophenyl-alanine", ChemBioChem, 2005, vol. 6, pp. 2147-2149.
Blight, S.K. et al., "Direct charging of tRNA$_{CUA}$ with pyrrolysine in vitro and in vivo", Nature, vol. 431, pp. 333-335.
Ohno, S. et al., "Site-selective Post-translational Modification of Proteins Using an Unnatural Amino Acid, 3-Azidotyrosine", J. Biochem, 2007, vol. 141, pp. 335-343.
Liu, W. et al., "Genetic incorporation of unnatural amino acids into proteins in mammalian cells", Nature Methods, 2007, vol. 4, pp. 239-244.
Office Action issued in Japanese application JP2009/533208 on May 14, 2013.
Shao et al., "Engineering new functions and altering existing functions", Current Opinion in Structural Biology, 1996, vol. 6, pp. 513-518.
Japan Office Action for Appl. No. 2009-533208 dated Apr. 1, 2014 (w/ English language translation).
Srinivasan, G. et al, "Pyrrolysine Encoded by UAG in Archaea: Charging of a UAG-Decoding Specialized tRNA," Science, May 24, 2002, vol. 296, pp. 1459-1462.

* cited by examiner

*Primary Examiner* — Kagnew H Gebreyesus
(74) *Attorney, Agent, or Firm* — Birch, Stewart, Kolasch & Birch, LLP

(57) ABSTRACT

Method for incorporating a lysine derivative (particularly an $N^\epsilon$-benzyloxycarbonyl-lysine (Z-Lys) derivative) having useful functional group such as heavy atom, selenium, reactive functional group, fluorescent group or crosslinker, which is suitable as a non-natural amino acid, into a desired protein in a site-specific manner. A mutant pyrrolysyl-tRNA synthetase has substitution of at least one amino acid residue selected from tyrosine residue at position 306, leucine residue at position 309 and cysteine residue at position 348 each constituting a pyrrolysine-binding site in the amino acid sequence for pyrrolysyl-tRNA synthetase of SEQ ID NO:2. The substitution of the amino acid residue is: of tyrosine residue at position 306 by glycine or alanine residue, of leucine residue at position 309 by glycine or alanine residue, and/or of a cysteine residue at position 348 by valine, serine or alanine residue.

14 Claims, 21 Drawing Sheets

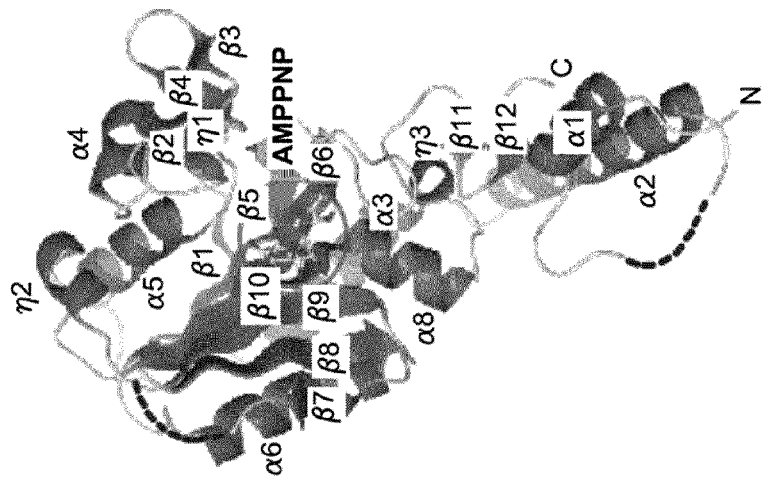
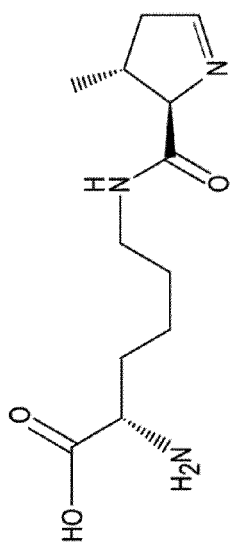
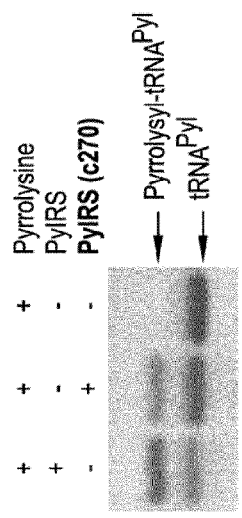
FIG.1A
FIG.1B
FIG.1C
FIG.1D $N^{\varepsilon}$-*o*-iodo-Z-Lys Z-aminoethyl-selenocysteine $N^{\varepsilon}$-*o*-ethynyl-Z-Lys $N^{\varepsilon}$-*o*-azido-Z-Lys $N^{\varepsilon}$-*o*-diaziryl-Z-Lys

US 8,735,093 B2

MUTANT PYRROLYSYL-TRNA SYNTHETASE, AND METHOD FOR PRODUCTION OF PROTEIN HAVING NON-NATURAL AMINO ACID INTEGRATED THEREIN BY USING THE SAME

REFERENCE TO RELATED APPLICATION

This application is based upon and claims the benefit of the priority of Japanese patent application No. 2007-243574, filed on Sep. 20, 2007, the disclosure of which is incorporated herein in its entirety by reference thereto.

TECHNICAL FIELD

The present invention relates to a mutant pyrrolysyl-tRNA synthetase, and a method for production of a protein having non-natural amino acid integrated therein by using the same. In further detail, the present invention relates to a method for site-specific incorporation of an $N^\epsilon$-benzyloxycarbonyl-lysine derivative into a protein of interest using *Methanosarcina*-derived mutant pyrrolysyl-tRNA synthetase and suppresser tRNA.

BACKGROUND ART

A non-natural amino acid-incorporated protein (alloprotein) which has a substitution of an amino acid residue at a desired position by an amino acid (a non-natural amino acid) other than 20 kinds of amino acids involved in normal protein synthesis could be an effective measure of analyzing the structure and function of a protein. Over 30 kinds of alloproteins have already been synthesized using aminoacyl-tRNA synthetase (aaRS)/tRNA pair derived from various biological species. A system which has most long history and is applied to incorporation of a lot of useful non-natural amino acids is a pair of a tyrosyl-tRNA synthetase (TyrRS) mutant and an amber-suppressed tRNA$^{Tyr}$. In this method, the following orthogonal relationship makes a key point: each of aaRSs in two groups of eubacteria and of archaebacteria and eukaryotes may aminoacylate tRNA in its group, whereas it could not aminoacylate tRNAs in the other group. For example, the TyrRS/tRNA$^{Tyr}$ pair of archaebacterium *Methanocaldococcus jannaschii* is an orthogonal pair in *E. coli* system, whereas the pair of *Escherichia coli* TyrRS and *Bacillus stearothermophilus* tRNA$^{Tyr}$ is an orthogonal pair in mammalian cell system. Therefore, these pairs may be used for extending genetic code in their systems (see, for example, Patent Document 1 and Non-Patent Document 1).

On the other hand, *Methanosarcina mazei*-derived pyrrolysyl-tRNA synthetase (PylRS) and amber suppressor tRNA$^{Pyl}$ function as orthogonal aaRS/tRNA pair in *E. coli* cells (see, for example, Non-Patent Document 2). Furthermore, it is reported that this pair may also be used for extending genetic code in eukaryotic cell (see, for example, Patent Document 2). Pyrrolysine is a lysine derivative having a bulky methylpyrroline moiety at the side chain. Wild-type PylRS may bind $N^\epsilon$-Boc-L-Lysine to tRNA$^{Pyl}$ in *E. coli* cells (see Patent Document 2). Moreover, X-ray crystal structure of a complex of wild-type PylRS, ATP analog, and pyrrolysine or pyrrolysine analog is reported (see Non-Patent Documents 3, 4 and 9).

[Patent Document 1] WO2004/070024
[Patent Document 2] Japanese Patent Kokai Publication No. JP-P2007-37445A
[Non-Patent Document 1] Sakamoto, K. et al., *Nucleic Acids Research*, 2002, Vol. 30, pp. 4692-4699.
[Non-Patent Document 2] Blight S. K. et al., *Nature*, (2004) Vol. 431, pp. 333-335.
[Non-Patent Document 3] Yanagisawa, T. et al., *Acta Cryst.* (2006) F62, 1031-1033
[Non-Patent Document 4] Kavran, J. M. et al., *Proc. Natl. Acad. Sci.* (2007) Vol. 104, pp. 11268-11273
[Non-Patent Document 5] Tsao, M.-L., Tian, F., Schultz, P. G. *ChemBioChem*. Vol. 2005, Issue 6, pp. 2147-2149
[Non-Patent Document 6] Ohno, S. et al., *J. Biochem.* (Tokyo) Vol. 141, pp. 335-343 (2007)
[Non-Patent Document 7] Mukai, et al., *Biochem. Biophys. Res. Commun.* Vol. 371, pp. 818-822 (2008)
[Non-Patent Document 8] Liu, W. et al., *Nat. Methods*. Vol. 4, pp. 239-244 (2007)
[Non-Patent Document 9] Yanagisawa, T. et al., *J. Mol. Biol.* (2008) 378, 634-652

SUMMARY

The entire disclosures of Patent Documents 1 and 2, and Non-Patent Documents 1-9 as mentioned above are incorporated herein by reference thereto. An analysis of related technology according to the present invention is given below.

A method for incorporating a tyrosine analog into a desired position of a protein using TyrRS/tRNA$^{Tyr}$ system is useful as a method for incorporating an amino acid containing a heavy atom for the phase determination due to the strict structure of a tyrosine analog with an aromatic ring. On the other hand, structural flexibility of a non-natural amino acid to be incorporated is required for incorporating a reactive amino acid with cross-linker, triple bond, double bond and the like into a protein and searching a target interacting with this protein in the cell. Therefore, it is thought that a lysine derivative having more flexible structure of its amino acid side chain is superior to a tyrosine analog. Generally, in order to modify the substrate specificity of lysyl-tRNA synthetase (LysRS), a method for incorporating a lysine derivative into a protein is used. However, LysRS has strict recognition of lysine so that, up to now, it is difficult to site-specifically incorporate a lysine derivative with a functional group of various sizes and forms into a protein. The present invention is aimed at providing a method for site-specifically incorporating into desired protein a lysine derivative, particularly an $N^\epsilon$-benzyloxycarbonyl-lysine (Z-Lys) derivative, which is suitable as a non-natural amino acid having a useful functional group such as a heavy atom, selenium, a reactive functional group, a fluorescent group, a crosslinker and the like.

The present invention is provided for solving the problem as mentioned above. The inventors found that a *Methanosarcina*-derived pyrrolysyl-tRNA synthetase is a unique aaRS which has low amino acid substrate specificity and is capable of activating not only pyrrolysine but also lysine derivatives with various hydrophobic functional groups. Furthermore, the inventors found a PylRS mutant capable of efficiently aminoacylating a Z-Lys derivative with bulky side chain structure. The present invention is completed on the basis of those findings.

That is, in a first aspect, the present invention provides a mutant pyrrolysyl-tRNA synthetase comprising a substitution of at least one amino acid residue selected from tyrosine at position 306, leucine at position 309, and cysteine at position 348, which constitute a pyrrolysine-binding site, in the amino acid sequence of the pyrrolysyl-tRNA synthetase set forth in SEQ ID NO:2. The substitution of the amino acid residue is: substitution of tyrosine at position 306 by glycine or alanine, substitution of leucine at position 309 by glycine or alanine, and/or substitution of cysteine at position 348 by valine, serine or alanine. In a preferable embodiment, the mutant pyrrolysyl-tRNA synthetase further comprises amino acid substitution of tyrosine at position 384 by phenylalanine or histidine.

In one preferable embodiment of the present invention, a mutant pyrrolysyl-tRNA synthetase is provided whose amino acid sequence comprises one or several amino acid deletion(s), substitution(s), or addition(s) at position(s) other than at positions 306, 309, 348 and 384, and which is capable of aminoacylating $N^\epsilon$-benzyloxycarbonyl-lysine. In a further different embodiment, a mutant pyrrolysyl-tRNA synthetase is provided which is obtained from a wild-type pyrrolysyl-tRNA synthetase, which is *Methanosarcina*-derived pyrrolysyl-tRNA synthetase that is a homolog of the amino acid sequence set forth in SEQ ID NO:2, so substituted that when the amino acid sequence of said homolog is aligned with the amino acid sequence set forth in SEQ ID NO:2, the homolog has substitution of alanine for tyrosine corresponding to position 306 of the amino acid sequence set forth in SEQ ID NO:2 and/or substitution of phenylalanine for tyrosine corresponding to position 384 thereof.

In another (second) aspect, the present invention provides an isolated DNA encoding the mutant pyrrolysyl-tRNA synthetase as well as an expression vector and a transformant containing the DNA, and the like.

In a further different (third) aspect, the present invention provides a method of producing a non-natural amino acid-incorporated protein wherein the following (a) to (c) are expressed in a cell or cell extract in the presence of an $N^\epsilon$-benzyloxycarbonyl-lysine derivative: (a) an aminoacyl-tRNA synthetase capable of activating the $N^\epsilon$-benzyloxycarbonyl-lysine derivative; (b) a suppressor tRNA capable of binding to the $N^\epsilon$-benzyloxycarbonyl-lysine derivative in the presence of said aminoacyl-tRNA synthetase, and (c) a gene encoding a desired protein that has nonsense mutation or frameshift mutation at a desired position. It is preferred that the $N^\epsilon$-benzyloxycarbonyl-lysine derivative is $N^\epsilon$-ortho-iodo-benzyloxycarbonyl-lysine; benzyloxycarbonyl-amino-ethyl-selenocysteine; $N^\epsilon$-ortho-ethinyl-benzyloxycarbonyl-lysine; $N^\epsilon$-ortho-azide-benzyloxycarbonyl-lysine; or $N^\epsilon$-ortho-diazyril-benzyloxycarbonyl-lysine.

In a furthermore different (fourth) aspect, the present invention provides a kit for synthesizing non-natural amino acid-incorporated protein comprising (a) cell extract; (b) a non-natural amino acid comprising $N^\epsilon$-benzyloxycarbonyl-lysine derivative; (c) the mutant pyrrolysyl-tRNA synthetase of the present invention; and (d) a suppressor tRNA capable of binding to an $N^\epsilon$-benzyloxycarbonyl-lysine derivative in the presence of said mutant pyrrolysyl-tRNA synthetase.

The PylRS mutant of the present invention has enhanced activity against Z-Lys with bulky side chain structure and derivatives thereof. Accordingly, it is possible to site-specifically incorporate a Z-Lys derivative efficiently into a desired protein in endogenous protein synthetic system of *E. coli*, animal cells and the like.

BRIEF DESCRIPTION OF THE DRAWINGS

In FIG. 1, (A) shows chemical structure of L-pyrrolysine; (B) shows domain structure of *M. mazei*-derived PylRS; (C) shows a result obtained from detection of pyrrolysine binding reaction to tRNA$^{Pyl}$ using PAGE and methylene blue staining; and (D) shows overall structure of PylRS (c270).

FIG. 3C shows a close-up view of the active site in PylRS (c270).

FIG. 3F shows a close-up view of the active site in PylRS (c270) in the case of pyrrolysine being an axial type stereoisomer.

PREFERRED MODES

[Pyrrolysyl-tRNA Synthetase (PylRS)]

Figure 2A:
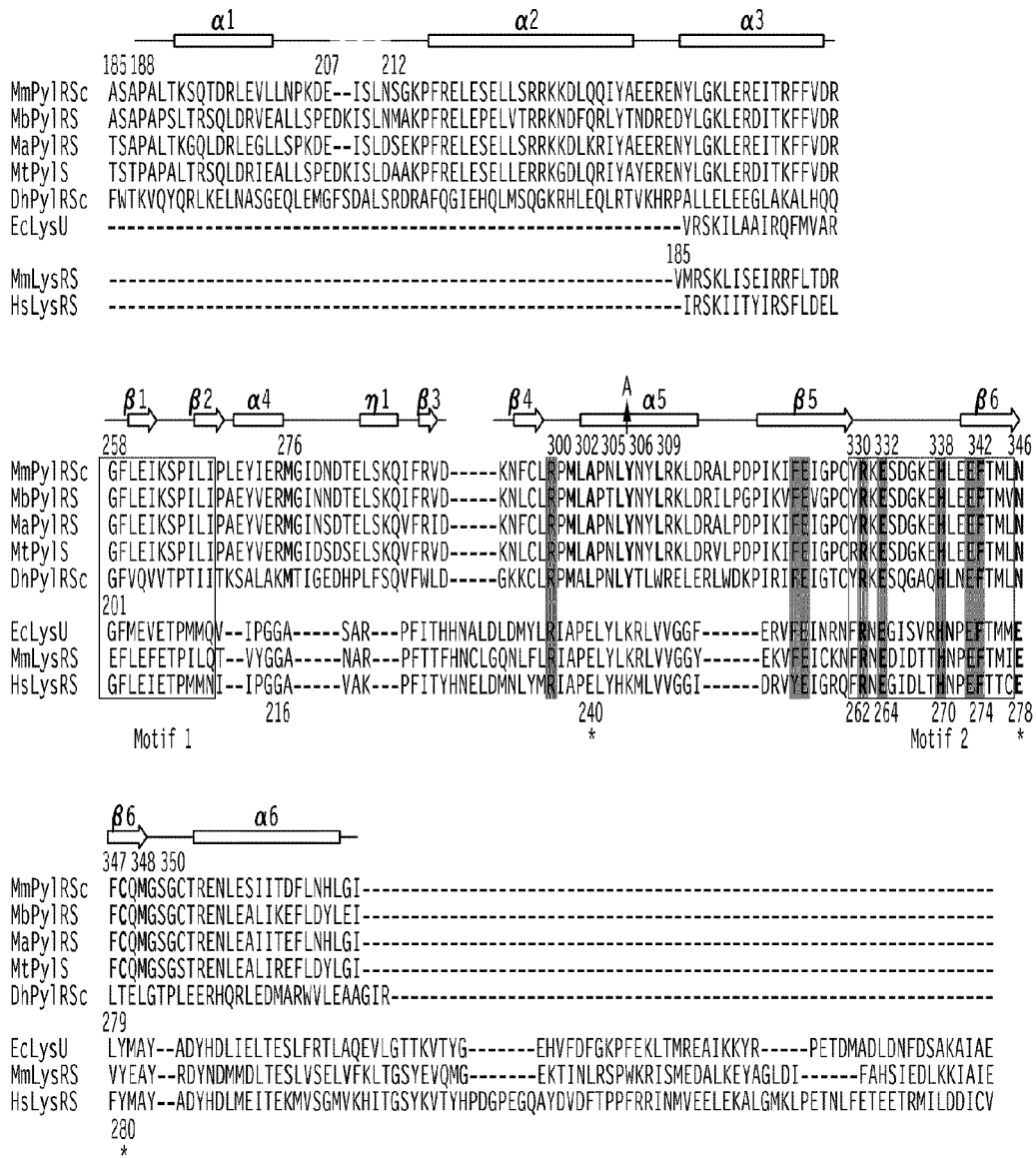
FIG. 2 shows tertiary structure-based sequence alignments between *M. mazei* PylRS (c270) and other PylRS and LysRS (SEQ ID NOS: 9-16).

Pyrrolysyl-tRNA synthetase (PylRS) of the present invention may be produced by mutagenesis, in various methods, of wild-type PylRS obtained from archaebacteria, particularly form methanogenic archaebacteria. Wild-type PylRS may be obtained from, but not restricted to, for example, *Methanosarcina mazei* (*M. mazei*), *Methanosarcina barkeri* (*M. barkeri*) and *Methanosarcina acetivorans* (*M. acetivorans*) and the like, which are methanogenic archaebacteria. Genomic DNA sequences of a lot of bacteria including those archaebacteria and amino acid sequences based on these nucleic acid sequences are known and it is also possible to obtain another homologous PylRS from public database such as GenBank by performing homology search for the nucleic acid sequences and the amino acid sequences, for example. *M. mazei*-derived PylRS, as typical examples, is deposited as Accession No. AAM31141, *M. barkeri*-derived PylRS is deposited as Accession No. AAL40867 and *M. acetivorans*-derived PylRS is deposited as accession No. AAM03608. *M. mazei*-derived PylRS as mentioned above is particularly preferred, the nucleic acid sequence of whose gene is shown in SEQ ID NO:1, and the amino acid sequence of whose protein is shown in SEQ ID NO:2. Sequences of PylRS homologs of the *Methanosarcina* are well conserved. For example, homology in amino acid sequences of the homologs is approximately 70% or more. Tertiary structures of these wild-type PylRSs are analyzed, and according to the method detailed below, PylRS mutants of the present invention are produced.

[Production of PylRS Mutants]

The present invention provides PylRS mutants which are produced on the basis of analysis of tertiary structure of catalytic domain in PylRS and a method for random mutagenesis. Concrete methods for crystallization of a complex of PylRS, substrate amino acids (pyrrolysine or Boc-Lys) and AMPPNP, which is an ATP analog, and for analysis of X-ray structure thereof are described below in Examples. As unit cell parameters of a crystal complex of *M. mazei*-derived PylRS catalytic domain, pyrrolysine and AMPPNP, space group is P6$_4$, unit cell is a=b=104.88 angstrom, c=70.43 angstrom, alpha=beta=90 degrees and lambda=120 degrees. Here, "unit cell" means a smallest and simple volume factor of crystal, and "space group" means symmetry of a unit cell. Methods for crystallization of catalytic domain of PylRS and for analysis of X-ray structure thereof have been already reported by the present inventors (see Non-Patent Document 3 as cited above, the entity of which is incorporated herein by reference).

For recognition of amino acid substrate by PylRS, it is important that a lysine derivative has a carbonyl which binds to its epsilon amino group and a hydrophobic functional group added to the end of the carbonyl. Wild-type PylRS may activate lysine derivatives in a case where the lysine derivatives have a hydrophobic functional group such as a pyrrole ring which has a certain degree of size and bulkiness. However, there is a limit to the size of lysine derivatives which can be activated by wild-type PylRS. For example, a lysine derivative with a large functional group, such as N$^\epsilon$-benzyloxycarbonyl-lysine (Z-Lys), cannot be incorporated into a protein. According to the PylRS mutant of the present invention, it is possible to incorporate Z-Lys, which is merely weakly activated by wild-type PylRS, into a protein efficiently.

Those PylRS mutants include a PylRS mutant comprising a substitution of at least one amino acid residue selected from tyrosine at position 306, leucine at position 309, and cysteine at position 348, which constitute a pyrrolysine binding site, in the amino acid sequence set forth in SEQ ID NO:2. Such amino acid substitution is preferably substitution of tyrosine at position 306 in SEQ ID NO:2 by an amino acid residue with comparatively small side chain structure, such as glycine, alanine, serine and threonine, more preferably substitution by glycine or alanine, most preferably substitution by alanine. Because an amino acid residue at position 306 in PylRS constitutes a substrate-binding site, it is thought to be preferable that the amino acid residue at position 306 is replaced with the above mentioned amino acid residues in order to avoid steric hindrance to binding of a substrate, particularly in a case where the substrate has a bulky side chain such as a Z group. Furthermore, leucine residue at position 309 may be replaced with glycine or alanine, preferably with alanine. In this case, it is preferable that cysteine at position 348 is also replaced with valine or alanine.

Further, it is preferable that tyrosine at position 384 in SEQ ID NO:2 is replaced with phenylalanine, valine, leucine, isoleucine, histidine and the like, more preferably with phenylalanine or histidine, most preferably with phenylalanine. In addition, glycine at position 131 may be replaced with glutamic acid. Although the effect of the above amino acid substitution on enhancement of activity is not necessarily evident, it is demonstrated that an amino acid residue at position 384 interacts with a substrate amino acid, particularly with the main chain part thereof (see Non-Patent Document 4). Therefore, there is likelihood that catalytic activity is enhanced independently of types of the substrate amino acid. Preferably this amino acid substitution at position 384 coexists with amino acid substitution at the above mentioned substrate-binding site, more preferably with amino acid substitution at position 306 or 309 as a double mutant, or with amino acid substitution at position 309 and 348 as a triple mutant.

In a preferable embodiment, the present invention provides a mutant PylRS comprising substitution of tyrosine residues at positions 306 and 384 by alanine and phenylalanine residues, respectively, in the amino acid sequence set forth in SEQ ID NO:2. This mutant PylRS (Y306A, Y384F) can efficiently aminoacylate a lysine derivative with bulky side chain structure such as Z-Lys. Herein, "being capable of aminoacylating" or "aminoacylation activity" means an activity for binding a lysine derivative to suppressor tRNA to synthesize aminoacyl tRNA. For example, it is possible to determine the amount of pyrrolysyl-tRNA (Pyl-tRNA) which is produced by purifying mutant enzyme and suppressor tRNA, and performing in vitro enzymatic reaction in the presence of ATP and a lysine derivative.

Usable methods for producing those mutants may include a variety of methods which are known to a person skilled in the art. For example, it is possible that using a primer that has substitution of nucleic acid sequence encoding the position of an amino acid of interest by nucleic acid sequence encoding an amino acid to be altered, a DNA that has substitution by nucleic acid sequence encoding the amino acid to be altered is amplified by PCR to obtain a DNA encoding a full length mutant PylRS, and the DNA is expressed using host cells such as *E. coli* cells. Alternatively, production of the mutants may be performed by known methods for site-specific mutagenesis, such as Kunkel method and Gapped duplex method. It is possible to use a kit for mutagenesis using these procedures (for example, Mutan-K, Mutan-G (TAKARA) and the like).

Further, the present invention includes a protein comprising amino acid sequence which has one or several amino acid deletions, substitutions, insertions or additions at positions other than at positions 306, 309, 348 and 384 in the amino acid sequence of the above-mentioned mutant PylRS, and which is capable of aminoacylating Z-Lys. "One or several amino acids" means approximately at most 5-10% of full length amino acid residues, for example, approximately 1-50 residues, preferably 1-20 residues, more preferably 1-10 residues, most preferably 1-5 residues. Likewise, the mutant PylRS of the present invention may have predetermined mutations at positions 306, 309, 348 and 384 in the above-mentioned amino acid sequence. As to the other amino acid residues, the mutant PylRS of the present invention may be of 70% or more homology, preferably of 80% or more homology, more preferably of 90% or more homology, as long as it maintains desired activity.

[Non-Natural Amino Acid]

As a non-natural amino acid used herein, for example, $N^\epsilon$-benzyloxycarbonyl-lysine (Z-Lys) derivative may be used. Z-Lys derivative is non-natural amino acid, and is suitably used as an amino acid which has reactive backbone having high flexibility comparing to those of tyrosine analog because the alkyl moiety in lysine side chain thereof serves as a linker. The Z group is generally known as a protecting group for peptide synthesis. However, the Z group is of high variability comparing to benzoyl (Bz) group and is of comparably high water solubility due to oxygen contained in its side chain. As a result, the Z group is easy to handle in aqueous conditions. In addition, since the Z group may be deprotected by catalytic hydrogen reduction which is a mild condition, it is possible that proteins which are linked with a crosslinker type Z-Lys derivative are separated in stable condition, and that a fluorescence probe etc. which is bound to a protein via the reactive functional group is, as necessary, cut off from the protein.

On the basis of binding models of Z-Lys to active sites in wild-type PylRS and mutant PylRS (Y306A), some preferable compounds may be obtained. It is expectable that ortho-position on the benzene ring of the Z group faces toward outside of the active site and thus does not easily cause steric hindrance. Therefore, substitution of a functional group which has comparative large size can be conducted. For example, Z-Lys derivatives with a crosslinker (azide, diazirine), a reactive functional group (alkyne) at the ortho-position, Z-Lys derivative with an atom for structural analysis phase determination (selenium) at the alkyl side chain etc. may be exemplified. In addition, the following are exemplified as Z-Lys derivative which may match with the substrate-binding site of PylRS mutant (Y306A): $N^\epsilon$-ortho-iodo-benzyloxycarbonyl-lysine, benzyloxycarbonyl-aminoethyl-selenocysteine, $N^\epsilon$-ortho-ethinyl-benzyloxycarbonyl-lysine, $N^\epsilon$-ortho-azide-benzyloxycarbonyl-lysine and $N^\epsilon$-ortho-diaziryl-benzyloxycarbonyl-lysine (see FIG. 12)

[Suppressor tRNA]

It is required that tRNA which is used in combination with the above-mentioned pyrrolysyl-tRNA synthetase (PylRS) should meet the following requirements that it is assigned to a nonsense codon other than codons assigned to natural amino acids of 20 kinds, and that it is recognized merely by the above-mentioned mutant PylRS but is not recognized by normal aminoacyl-tRNA synthetase in host (orthogonal tRNA), and should be expressed in eubacteria or mammalian cells. As such type of tRNA, archaea-derived suppressor tRNA is exemplified.

Here, as nonsense codons, UAG (amber), UAA (ochre), UGA (opal) are exemplified, it is preferable that UAG (amber) or UGA (opal) are used. As an alternative to the nonsense codons, a codon consisting of 4 or more bases (preferably 4 or 5 bases) (hereinafter referred to as "frameshift codon") may be used.

Those tRNAs may be prepared by, for example, obtaining a gene corresponding to tRNA$^{Pyl}$ from the above-mentioned archaebacteria genome, and expressing in vitro or in vivo this gene directly or after introduction of desired mutation. As an example, *M. mazei*-derived wild-type tRNA has the following nucleic acid sequence:

tRNA$^{Pyl}$:

(SEQ ID NO: 3)
5'-GGAAACCUGAUCAUGUAGAUCGAAUGGACUCUAAAUCCGUUC
AGCCGGGUUAGAUUCCCGGGGUUUCCGCCA-3'.

[DNA Encoding Mutant PylRS of the Present Invention, Expression Vector Comprising this DNA, and Transformant]

The present invention includes DNA encoding mutant PylRS which is obtained by the above-mentioned manner. In a preferable embodiment, DNA of the present invention includes DNA comprising substitution of codons (TAC) and (TAT), which each correspond to tyrosine, at positions 306 and 384 by codon (GCT, GCC, GCA or GCG), which corresponds to alanine, and codon (TTT or TTC), which corresponds to phenylalanine, respectively, in the DNA encoding wild-type PylRS set forth in SEQ ID NO:1. In addition, codon of an amino acid at position 306 may be a codon (GGT, GGC, GGA or GGG) corresponding to glycine, and a codon of an amino acid at position 384 may be a codon (CAT or CAC) corresponding to histidine.

Further, the DNA of the present invention includes DNA which has at least 80% or more, preferably 90% or more, further preferably 95% or more homology with the DNA consisting of the nucleic acid sequence set forth in SEQ ID NO:1 in the case of calculation in default condition by BLAST and the like; and whose codons of the amino acid chain at positions 306 and 384 are codons corresponding to alanine and phenylalanine, respectively. Furthermore, RNAs corresponding to the above-mentioned DNA, for example, mRNA transcribed from the DNA or antisense RNA and the like, are also included in the present invention.

The DNA of the present invention also includes DNA which hybridizes under stringent condition with DNA comprising sequence complementary to the above-mentioned DNA and encodes mutant PylRS capable of aminoacylating $N^\epsilon$-benzyloxycarbonyl-lysine. Here, "hybridize under stringent condition" is an experimental condition well-known to a person skilled in the art. Concretely, "stringent condition" is a condition which allows identification in such a manner as to perform hybridization in the presence of 0.7-1 M of NaCl at ca. 60-68 degrees Celsius, followed by washing at ca. 65-68 degrees Celsius using 0.1-2×SSC solution (wherein "1×SSC" comprises 150 mM of NaCl and 1.15 mM of sodium citrate). For selecting stringency, in the washing step, salt concentration and temperature may be optimized as necessary. In addition, it is a common technical knowledge of a person skilled in the art to add formamide, SDS and the like for increasing stringency.

The present invention also includes an expression vector capable of expressing mutant PylRS by link (insert) of the DNA of the present invention. A vector for insertion of the DNA of the present invention includes any vectors that may be replicated in hosts and includes, but is not particularly restricted to, plasmid DNA, bacteriophage DNA and the like. In the expression vector of the present invention, preferably, the DNA of the present invention is integrated into the vector such that when the vector is introduced into host cells, the above-mentioned mutant PylRS may be produced in the host cells. Accordingly, to the vector of the present invention may be linked DNA which contains, in addition to promoters (for example, T7 promoter, CMV promoter, trp promoter, lac promoter, PL promoter, tac promoter and the like), cis element such as enhancer, splicing signal, poly A attachment signal, selection marker, ribosome binding sequence (SD sequence) and the like is linked, as necessary. As a selection marker, for example, dihydrofolate reductase gene, ampicillin resistance gene, neomycin resistance gene and the like are exemplified.

The present invention includes transformant, preferably eubacteria and eukaryotic cell, which was transformed with the expression vector of the present invention. Herein, "eubacteria" includes bacteria which belong to, for example, *Escherichia* such as *Escherichia coli* (*E. coli*), *Bacillus* such as *Bacillus subtilis*, *Pseudomonas* such as *Pseudomonas putida*, *Rhizobium* such as *Rhizobium meliloti*. Further, "eukaryotic cell" includes yeasts such as *Saccharomyces cerevisiae* and *Schizosaccharomyces pombe*, and animal cells such as COS cell and CHO cell. Transformation may be performed by a known method such as, for example, a method using calcium ion (Cohen, S. N. et al. (1972) *Proc. Natl. Acad. Sci.*, USA 69, 2110-2114), DEAE-dextran method, electroporation method and the like.

[Production of Z-Lys Derivative-Incorporated Protein]

Mutant PylRS thus obtained may be used for production of Z-Lys derivative-incorporated protein, in vitro or in vivo, in combination with suppressor tRNA derived from archaea or eukaryote. That is, the present invention provides a method of producing a Z-Lys derivative-incorporated protein including expressing (a) an aminoacyl-tRNA synthetase for the Z-Lys derivative, (b) a suppressor tRNA capable of binding to the Z-Lys derivative in the presence of the aminoacyl-tRNA synthetase, and (c) a gene encoding a desired protein that has a nonsense mutation or frameshift mutation at a desired position in a cell or cell extract in the presence of the Z-Lys derivative.

Here, a synthesis system for PylRS and suppressor tRNA includes any expression system, and, for example, includes, but is not particularly restricted to, cell-free protein synthesizing system, protein synthesizing system in cells of eubacteria, and eukaryotic cells, preferably animal cells, particularly preferably mammalian cells.

The cell-free protein synthesizing system is a system for synthesizing a desired protein by obtaining protein factors required for translation of protein as a form of cell extract, followed by reconstituting this reaction in vitro. The cell-free system may be constituted using extracts derived from various biological species. For example, the following may be used: extracts of eukaryotic cells and prokaryotic cell under conditions of high protein synthesizing activity, such as, for example, bacteria such as *E. coli* and thermophilic bacterium, wheat germ, rabbit reticulocyte, mouse L-Cell, Ehrlich ascites carcinoma cell, HeLa cell, CHO cell, and budding yeast (Clemens, M. J., *Transcription and Translation—A Practical Approach*, (1984), pp. 231-270, Henes, B. D. et al. eds., IRL Press, Oxford).

Usable extracts from *E. coli* may include S30 extract prepared by the method disclosed in Zubay et al. (*Ann. Rev. Genet.* Vol. 7, pp. 267-287 (1973)) or Pratt, J. M. et al., (*Transcription and Translation—A Practical Approach*, (1984), pp. 179-209, Henes, B. D. et al. eds., IRL Press, Oxford)). *E. coli* S30 extract contains all enzymes and factors of *E. coli* cells required for transcription and translation. Furthermore, supplemental liquid mixture may be added. In a concrete preparation method: first, *E. coli* cells are is cultured to collect the cells using centrifugation and the like; the collected cells are washed to be re-suspended in buffer, followed by destructing them using French press, glass beads, Waring blender and the like; insoluble substances of destructed *E. coli* cells are removed using centrifugation, followed by mixing the remainder with pre-incubation liquid mixture to be incubated, thereby endogenous DNA and RNA being degraded, in addition to which endogenous nucleic acids may be degraded by adding calcium salt, nuclease from *Micrococcus* and the like; subsequently, endogenous amino acids, nucleic acids, nucleosides and the like are removed using dialysis, followed by aliquoated and stored in liquid nitrogen or at ca. −80 degrees Celsius.

In the case of performing reaction of synthesizing Z-Lys derivative-incorporated protein, the cell extracts as mentioned above may contain DNA or RNA which encodes a desired protein that has nonsense mutation or frameshift mutation at a desired position of transcription/translation templates; amino acids which include Z-Lys derivative; mutant PylRS of the present invention; suppressor tRNA which is capable of binding to Z-Lys derivative in the presence of the mutant PylRS; energy source; a variety of ions; buffer; ATP regenerating system; nuclease inhibitor, tRNA, reducing agent; polyethylene glycol; cAMP; folates and antimicrobial agent, and, in cases where DNA is used as template, the cell extracts as mentioned above may include further substrate for RNA synthesis and RNA polymerase and the like. These elements are selected and prepared as required according to types of proteins of interest and protein synthesizing systems to be used. For example, in the case of S30 extract of *E. coli* cells, a part or all of the following materials are added: Tris-acetate, DTT, NTPs (ATP, ACT, GTP and UTP), phosphoenolpyruvate, pyruvate kinase, amino acids (phosphoserine is added in addition to 20 kinds of natural amino acids), polyethylene glycol (PEG), folic acid, cAMP, tRNA, ammonium acetate, potassium acetate, potassium glutamate, magnesium acetate at suitable concentration etc.

For expressing mutant PylRS in mammalian cells, the following may be performed: DNA sequence of *M. mazei*-derived wild-type PylRS gene with Histidine-tag etc. at N terminus region thereof is amplified using PCR; this DNA sequence is integrated into an expression vector such as commercially available pcDNA3.1 (Invitrogen) at NheI-BamHI site; and the constructed plasmid is introduced into mammalian cells. Methods for introducing a vector into cells may include, for example, electroporation, calcium phosphate method, lipofection and the like.

On the other hand, methods for expressing suppressor tRNA are not restricted to particular ones, so suppressor tRNA may be expressed in eubacteria such as *E. coli*, or in eukaryotic cells such as mammalian cells according to methods known to a person skilled in the art. In the case of expression in *E. coli* cells, for example, promoter sequence and terminator sequence are linked at 5' terminus and 3' terminus, respectively, of DNA encoding suppressor tRNA. Type-II promoter transcripting tRNA in eukaryotic cells is an internal promoter comprising 2 regions in tRNA cording sequence, consensus sequences of which are known as box A and box B. Consensus sequence of box A is TRGCNNAGYNGG (SEQ ID NO:7) at positions 8-19, and consensus sequence of box B is GGTTCGANTCC (SEQ ID NO:8) at positions 52-62. Accordingly, in a case where, for example as is the case of suppressor tyrosine tRNA of *Bacillus stearothermophilus*, the cording sequence has box A and box B, suppressor tRNA can be expressed in animal cells without any modification. In contrast, in a case where suppressor tRNA has no internal promoter, the suppressor tRNA can be expressed using an external promoter in eukaryotic cells. For example, suppressor tRNA may effectively be expressed in animal cells by binding tRNA nucleic acid sequence or promoter sequence of U1 or U6 snRNA gene of eukaryote to suppressor tRNA gene at 5' terminus thereof. In further different embodiments, suppressor tRNA may be coexpressed together with T7 RNA polymerase in animal cells by linking T7 phage-derived T7 promoter.

Further, the present invention provides a kit for synthesizing Z-Lys derivative-incorporated protein comprising (a) cell extract as mentioned above, (b) a non-natural amino acid comprising $N^\epsilon$-benzyloxycarbonyl-lysine derivative, (c) the mutant PylRS of the present invention; and (d) a suppressor tRNA capable of binding to Z-Lys derivative in the presence of the mutant PylRS.

The "non-natural amino acid" as mentioned at (b) may be a mixture with 20 kinds of natural amino acids. These components may be aliquoted for usability and be delivered as a kit for synthesizing Z-Lys derivative-incorporated protein. These products may be preserved in frozen or dried form, and marketed as a kit accommodating them in a container suitable for preservation and delivery. Instructions and vector DNA etc. may be enclosed in the kit.

EXAMPLE 1

[Preparation and Crystallization of Sample]

L-pyrrolysine: $N^6$-[(2R,3R)-3-methyl-3,4-dihydro-2H-pyrrole-2-ylcarbonyl]-L-lysine (see FIG. 1A) was chemically synthesized and its chemical structure was confirmed using $^1$H-NMR. Various derivatives of L-lysine were purchased from Bachem AG (Switzerland). *M. mazei*-derived tRNA$^{Pyl}$ was synthesized by in vitro transcription and purified using RESOURCE Q column chromatography (Amersham Biosciences Inc.).

The full length PylRS derived from *M. mazei* is a protein of molecular weight 51 kDa which consists of 454 amino acid residues. The gene encoding this full length PylRS was amplified using the following primers from genomic DNA of *M. mazei* JCM9314 strain (RIKEN BioResource Center) and cloned into a vector plasmid pET28c (Novagen Inc.) at NdeI-SacI site. This vector was introduced into *E. coli* cells to express a protein, at the N terminus of which was linked

```
pET28-derived His-tag cording region
                                    (SEQ ID NO: 4)
(MGSSHHHHHHSSGLVPRGSH).

N-terminal primer:
                                    (SEQ ID NO: 5)
5'-AGGGGTAACCATATGGATAAAAAACCACTAAACAC-3'

C-terminal primer:
                                    (SEQ ID NO: 6)
5'-ACATGGTCCAGAGCTCTTACAGGTTGGTAGAAATCCCGTT-3'
```

On the other hand, although the full length PylRS was expressed in *E. coli* cells and its crystal was prepared, no crystal suitable for X-ray structural analysis was obtained. Accordingly, PylRS of which the 184 amino acids from the N terminus were truncated (hereinafter referred to as "PylRS (c270)"; see FIG. 1B) was produced. At the N terminus of the PylRS (c270) protein was linked 6 repeats of Histidine-tag to produce a fusion protein, which was expressed in *E. coli* BL21 (DE3) CodonPlus-RIL strain (Stratagene Inc.). According to the method disclosed in the above-mentioned Non-Patent Document 3, the native PylRS (c270) protein and a selenomethionine-labeled PylRS (c270) protein were purified and crystallized. In order to obtain better crystal, crystallization was conducted under slightly altered conditions, as follows: Cocrystal of PylRS (c270) was obtained at ca. 20 degrees Celsius within 3 minutes in 50 mM sodium cacodylate (pH 7.0) containing 5% PEG4000 (or PEG3350) and 5 mM of MgCl$_2$ in the presence of 5 mM of pyrrolysine (or 3.45 mM of Boc-Lys) and 5 mM of AMPPNP.

[Collection of Data]

According to the method disclosed in the above-mentioned Non-Patent Document 3, collection of data for X-ray crystal structural analysis was performed. Using Beamline BL41XU in SPring-8, 1.8 angstrom data set from a crystal complex of PylRS(c270)/pyrrolysine/AMPPNP and 1.79 angstrom data set from a crystal complex of PylRS(c270)/Boc-Lys/AMP-PNP were collected.

[Structural Analysis]

MAD method was used to determine phase. Using SnB, 5 of 7 selenium substitution sites were localized to calculate initial phase using SOLVE. The initial phase was improved with density modification using RESOLVE. A partial model was constructed automatically by RESOLVE, and the remainder was constructed with Program O mainly and refined by CNS. Quality of conformational structural model was analyzed using PROCHECH.

[Aminoacylation Assay]

Mutagenesis of wild-type PylRS was performed using QuikChange Mutagenesis Kits (Stratagene Inc.). The full length PylRS mutant was overexpressed in *E. coli* cells, and then purified using HisTrap column (Amersham Biosciences Inc.). Aminoacylation reaction was performed at ca. 37 degrees Celsius for 1 h. The reaction solution for aminoacylation comprises 2.83 µM of purified PylRS derived from *M. mazei* (or 9 µM of PylRS (c270)), 10 mM of MgCl$_2$, 2 mM of ATP, 4 mM of DTT, 2.11 µM of transcript of *M. mazei*-derived tRNA$^{Pyl}$, and adequate amount of concentrated solution of a variety of amino acids dissolved in 100 mM of HEPES buffer (pH 7.2). Acid-urea polyacrylamide gel electrophoresis was used to analyze whether tRNA had been aminoacylated or not.

[Entire Structure]

The PylRS of *M. mazei* consists of 454 amino acid residues and has high homology with PylRS of *M. barkeri* (74% identity). The PylRS is mainly made up of 2 domains. The C-terminal domain having approximately 250 amino acid residues is of sequence homology with Class-II aminoacyl-tRNA synthetase, whereas the N-terminal domain having approximately 140 amino acid residues is unique (see FIG. 1B). The PylRS(c270) corresponding to an aminoacyl-tRNA synthetase-like domain may esterify tRNA$^{Pyl}$ with pyrrolysine (see FIG. 1C). For crystal growth of this PylRS(c270), ATP analogue needs to be added. In this regard, it is considered that ATP binds tightly to PylRS (c270) to stabilize the structure thereof.

First, structure of AMPPNP-bound PylRS (c270) was determined by multi-wavelength anomalous dispersion method (MAD method) using selenomethionine-substituted one. The conformational structure thereof had the distinctive feature of Class-II aaRS including lysyl-tRNA synthetase (LysRS). In the PylRS (c270) structure, the residues at positions 195-237 from N-terminus formed two α-helices (α1 and α2), and the residues at positions 241-432 constituted a catalytic domain (see FIG. 1D). The catalytic domain had an extended seven anti-parallel beta-sheets (β1, β5, β6, β7, β8, β9, and β10) and an α-helix surrounding them, and showed a characteristic topology of the class-II aaRSs.

Figure 2B:
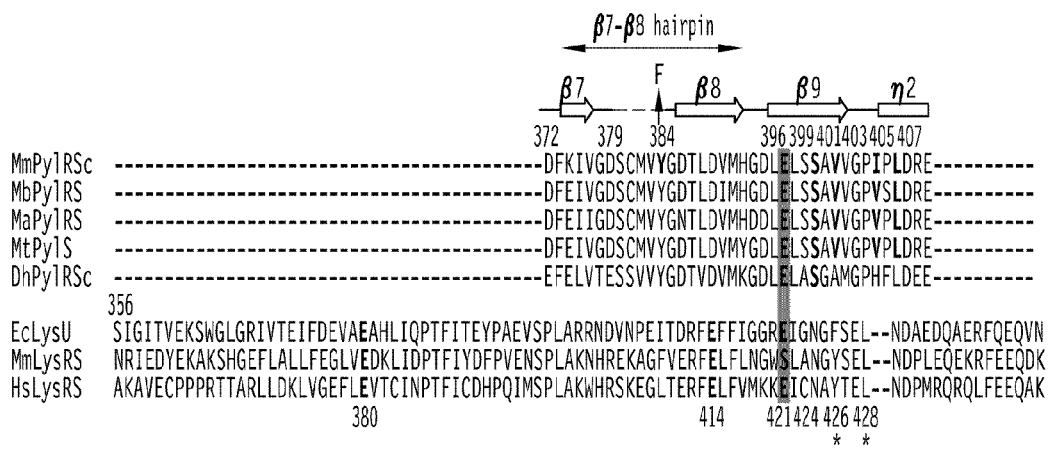
Figure 2B:
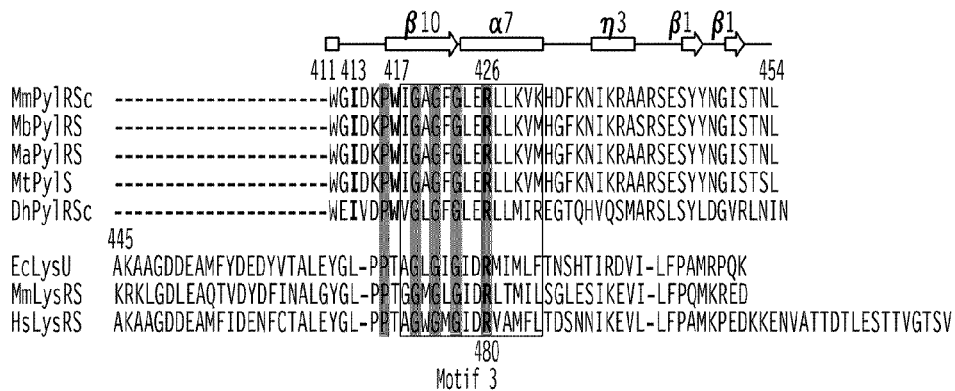

FIG. 2 shows sequence alignments based on the conformations between *M. mazei* PylRS(c270), and other PylRS and LysRS. The sequences were aligned using the program CLUSTAL W, and partially optimized manually. Highly conserved amino acid residues between PylRS and LysRS were surrounded with square frames. The secondary structures were schematically represented at the upper side of the aligned sequences. The amino acid substitution sites of tyrosine residue at position 306 and tyrosine residue at position 384 relating to the present invention were indicated with arrows. The numerals at the upper side of the aligned sequences represent the positions of amino acid residues of *M. mazei* PylRS (c270), and the numerals at the lower side of the aligned sequences represent those of *E. coli* LysRS. MmPylRSc represents *Methanosarcina mazei* PylRS (c270); MbPylRS represents *Methanosarcina barkeri* PylRS (AAL40867); MaPylRS represents *Methanosarcina acetivoran* PylRS (AAM03608); MtPylRS represents *Methanosarcina thermophila* PylRS; DhPylRSc represents *Desulfitobacterium hafniense* PylRS (AAU93507); EcLysU represents *E. coli* LysRS (AAA97029); MmLysRS represents *Methanosarcina mazei* Class-II LysRS (AAK29404); and HsLysRS represents human cytoplasmic LysRS (AAH04132).

[Recognition of Pyrrolysine and ATP]

Figure 3A:
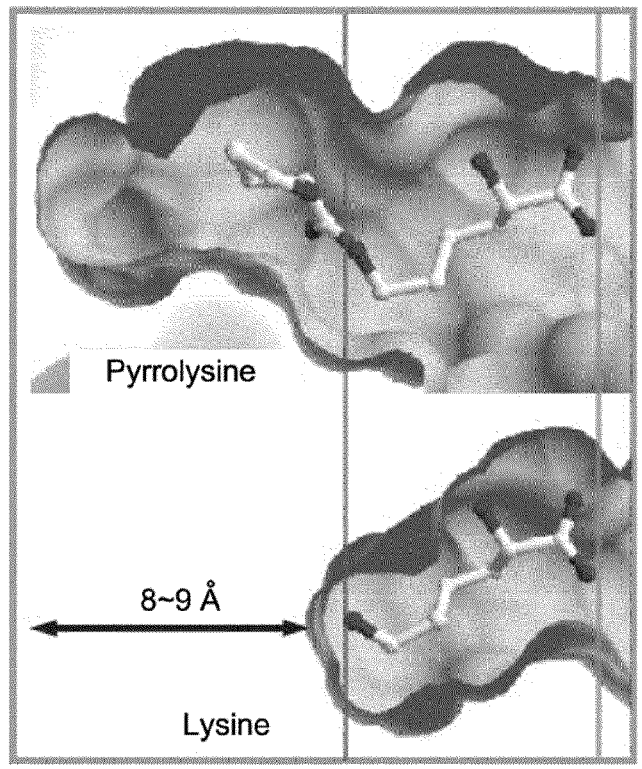
FIG. 3A shows comparison between an active site of PylRS (c270) (see.
Figure 3B:
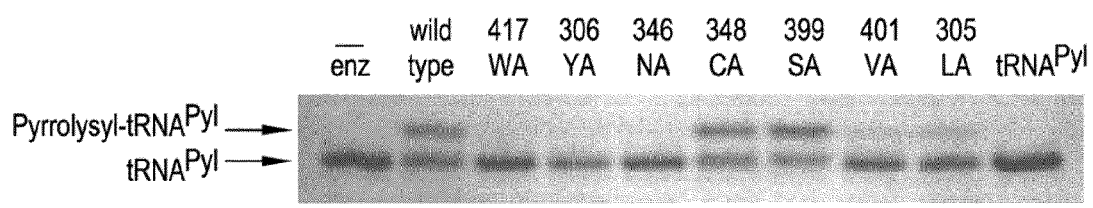
FIG. 3B shows a result obtained from research of effect of mutation incorporated at the active site of PylRS (c270) on aminoacylation reaction of pyrrolysine.
Figure 3C:
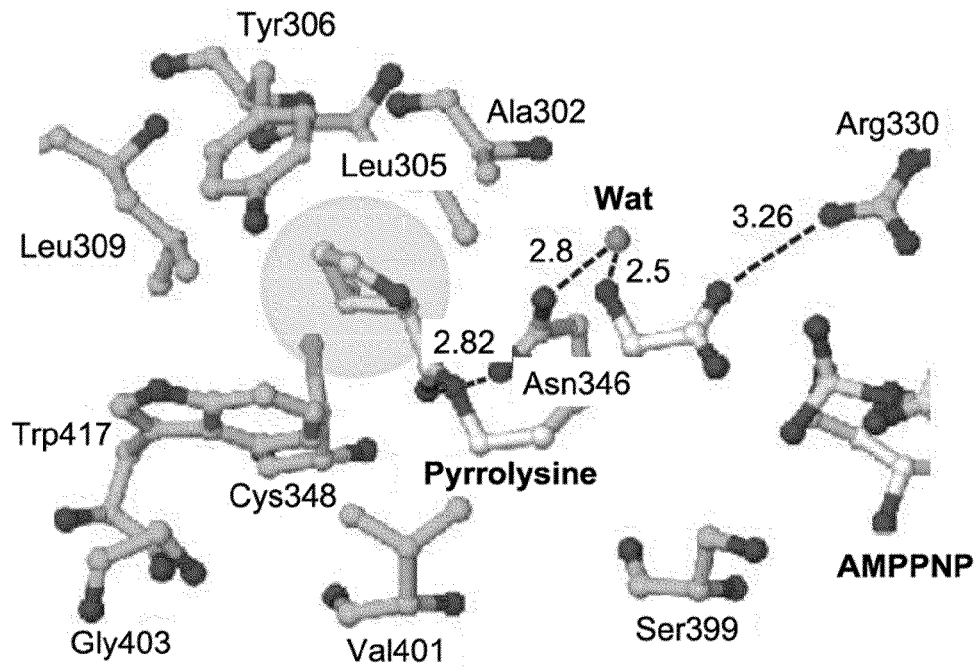
FIG. 3C) and an active site of LysRS (see FIG. 3D).
Figure 3D:
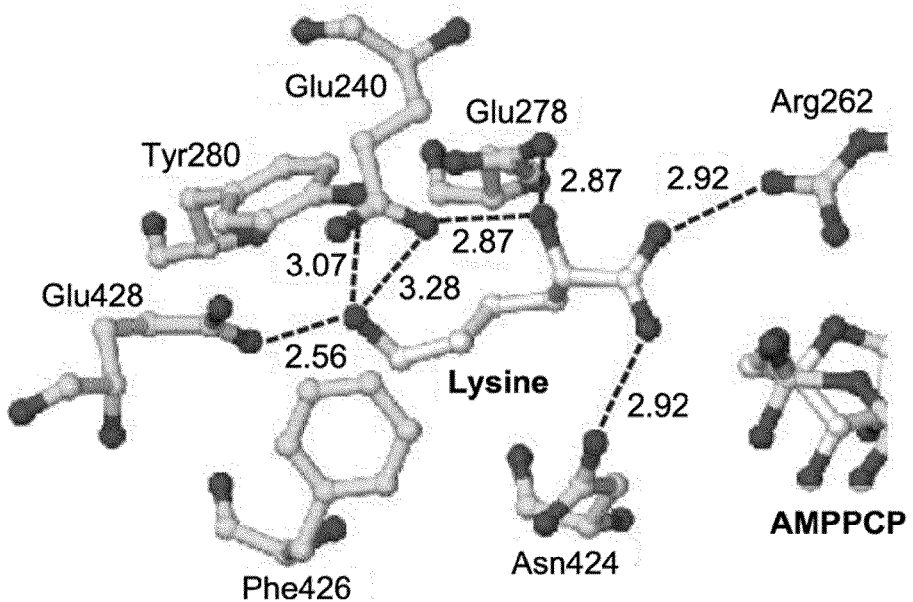
FIG. 3D shows a close-up view of the active site in LysRS.
Figure 3E:
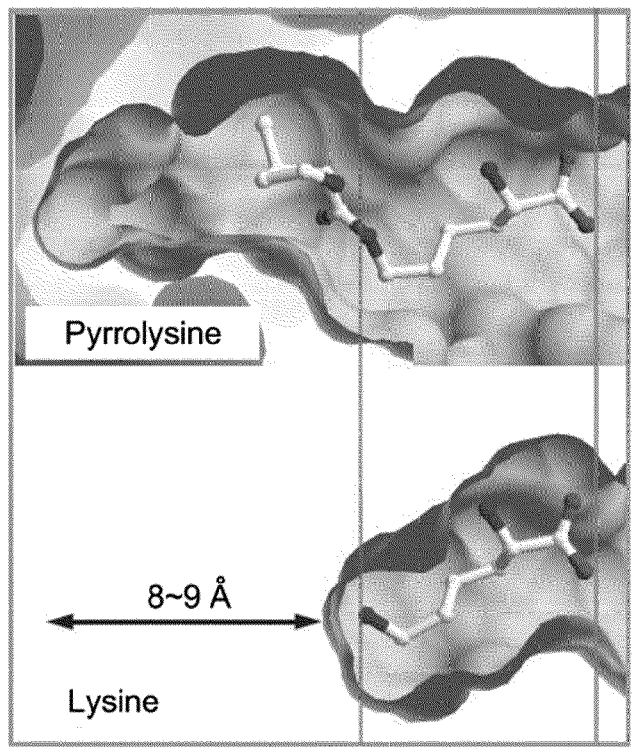
FIG. 3E shows comparison between an active site of PylRS (c270) (see.
Figure 3F:
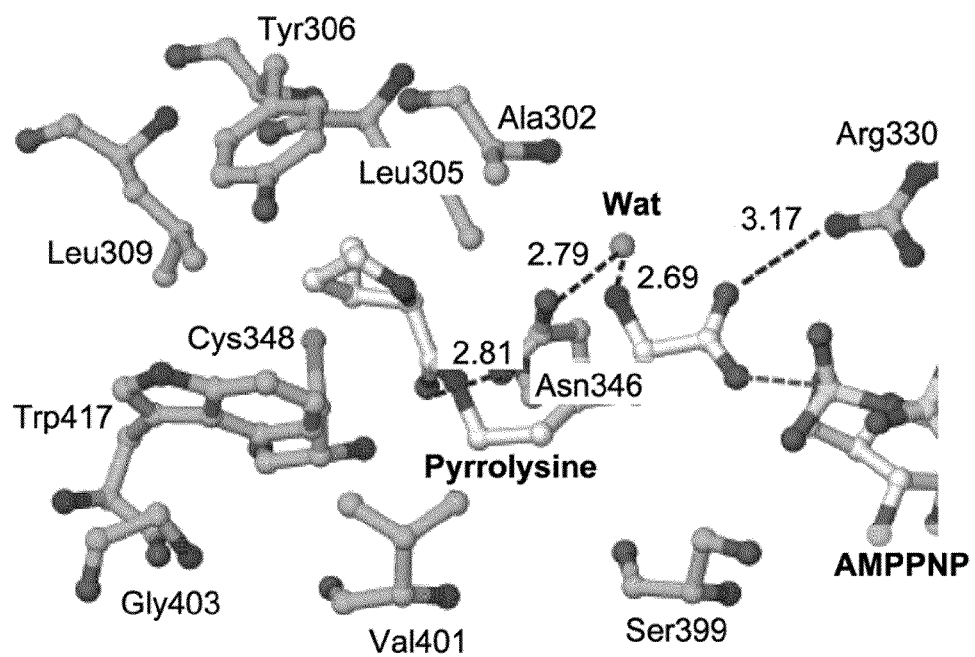
FIG. 3F) and an active site of LysRS (see FIG. 3D) in the case of pyrrolysine being an axial-type stereoisomer.

Next, from the crystal structure of PylRS(c270) complexed with pyrrolysine and AMPPNP, it was found that the amino acid-binding site of the PylRS was much larger than that of the normal aminoacyl-tRNA synthetase. The pyrrolysine molecule was bound on the surface of 7 antiparallel β-sheets distinctive of the Class-II aminoacyl-tRNA synthetase. Bulky 4-methyl-pyrroline ring is accommodated in a tunnel, which is mainly formed by hydrophobic residues, including Ala-302, Leu-305, Tyr306, Leu309, Cys348, Val-401, Leu-407, Ile-413, and Trp417 (see FIGS. 3A and 3C). The amide moiety of the Asn-346 side chain faces to an amino acid substrate and forms a hydrogen bond at a distance of 2.82 angstrom with the side-chain carbonyl group of the pyrrolysine to fix the position thereof. In contrast, in a case where pyrrolysine is an axial type stereoisomer, the distance between the amide moiety of the Asn-346 side chain and the side-chain carbonyl group of the pyrrolysine was 2.81 angstrom (see FIGS. 3E and 3F). Further, the carbonyl group of the Asn-346 side chain binds indirectly to the alpha-amino group of the pyrrolysine with a hydrogen bond through a water molecule. The guanidium group of Arg-330 highly conserved binds to the α-carbonyl group of pyrrolysine with a hydrogen bond. There are no hydrogen bonds other than these 3 hydrogen bonds at Asn-346 and Arg-330. This amino acid recognition mechanism of PylRS is very distinctive (see FIG. 3C). The aminoacylation activities of the PylRS mutants comprising a substitution at any one of amino acid residues which form the tunnel accommodating the pyrrolysine were determined, resulting in that the activities of the 5 mutants, in which alanine was substituted correspondingly for leucine at position 305, tyrosine at position 306, asparagine at position 346, valine at position 401 and tryptophan at position 417 were decreased drastically (see FIG. 3B).

[Comparison Between the Active Sites of the PylRS and the LysRS]

The structure of the PylRS and its substrate binding mechanism were compared with those of *Escherichia coli* LysRS. In the active site of *E. coli* LysRS, highly conserved residues (Glu-240, Arg-262, Glu-278, Tyr-280, Asn-424, Phe-426, and Glu-428) are involved in L-lysine recognition (see FIG. 3D). In a case where these residues are mutagenized, Km value for L-lysine which is a substrate of LysRS is increased drastically. On the contrary, Arg-262 is merely conserved in *M. mazei* PylRS(c270), and the other positions are occupied by smaller, uncharged amino acid residues (Ala-302, Asn-346, Cys348, Ser-399, Val-401, and Gly-403). By these amino acid substitutions, the amino acid-binding site (tunnels) in PylRS is 8 to 9 angstrom deeper than that of the L-lysine-binding pocket in LysRS (see FIG. 3A). As described above, only 3 hydrogen bonds are formed between pyrrolysine and PylRS (c270), whereas at least 7 hydrogen bonds are formed between L-Lys and LysRS. The small number of hydrogen bonds interacting with the lysine moiety makes it difficult for PylRS to activate L-lysine as a substrate. Actually, PylRS activates tRNA$^{Pyl}$ with pyrrolysine at a concentration of 1 mM, whereas it cannot activate 20 kinds of normal amino acids including lysine even at a concentration of 0.5 M. Intriguingly, in pyrrolysine recognition by PylRS, a moiety corresponding to the lysine side chain serves as a spacer between the main chain and the methyl-pyrroline carbonyl moiety. The deep hydrophobic tunnel and weak recognition of the lysyl moiety are great differences between PylRS and LysRS in substrate recognition.

[Activation of Non-natural Amino Acids by PylRS]

Figure 4A:
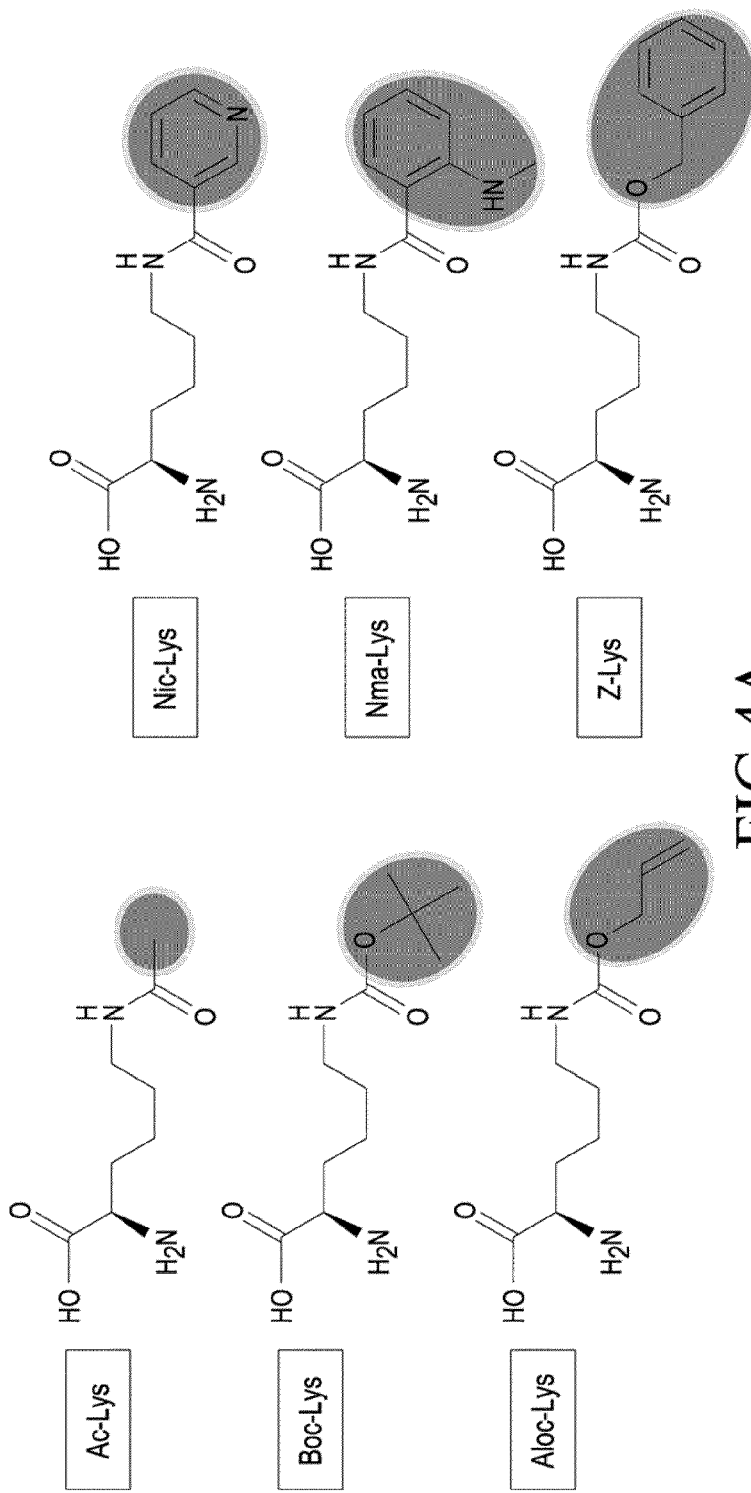
In FIG. 4, (A) shows chemical structures of the lysine derivatives; and (B) shows results obtained from analysis of aminoacylation reaction of these derivatives using acidic urea PAGE.
Figure 4B:
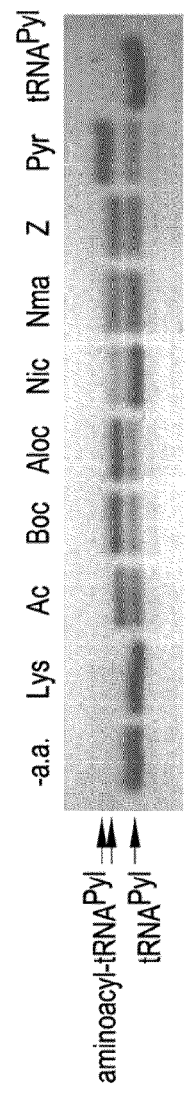

From the conformational structure of the substrate recognition site of the PylRS, it was surmised that PylRS could activate non-natural amino acid other than pyrrolysine. Based upon this hypothesis, it was examined whether PylRS could activate 6 kinds of N$^ε$-lysine derivatives shown in FIG. 4A. The results were shown in FIG. 4B. In each lane, aminoacylation was conducted in the presence of PylRS under the following condition (which is shown starting from the left column): no amino acid; 0.5 M Lys; 100 mM Ac-Lys; 1 mM Boc-Lys; 1 mM Aloc-Lys; 10 mM Nic-Lys; 7 mM Nma-Lys; 3.5 mM Z-Lys; 1 mM pyrrolysine; and control tRNA$^{Pyl}$. As demonstrated in FIG. 4B, tert-butyloxycarbonyl-lysine (Boc-Lys) and allyloxycarbonyl-lysine (Aloc-Lys) were activated at a concentration of 1 mM, as efficiently as pyrrolysine. Furthermore, it was found that the wild-type PylRS esterified tRNA$^{Pyl}$ with N$^ε$-modified lysine derivatives, such as N$^ε$-acetyl-L-lysine (Ac-Lys), N$^ε$-nicotinoyl-L-lysine (Nic-Lys), N$^ε$-benzyloxycarbonyl-L-lysine (Z-Lys), N$^ε$-(N-methyl-anthraniloyl)-L-lysine (Nma-Lys) which was a fluorescent amino acid, and the like. On the contrary, wild-type PylRS could not activate lysine derivatives which were N$^ε$-linkaged with methyl, dimethyl, trimethyl, isopropyl, dansyl, o,p-dinitrophenyl, p-azidobenzoyl, biotinyl, 9-fluorenylmethoxycarbonyl, and p-toluenesulfonyl groups. Accordingly, it was found that PylRS could recognize N$^ε$-substituents having bulkiness at a certain range.

Figure 5A:
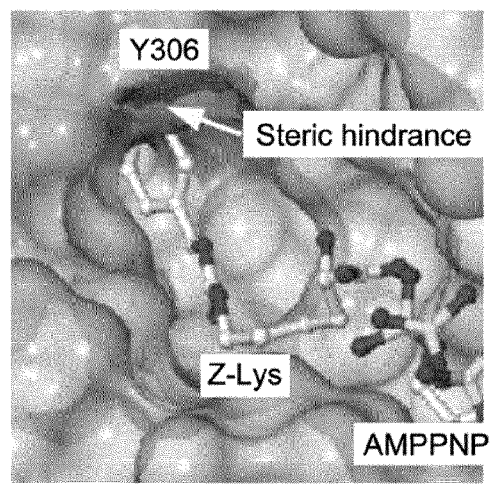
In FIG. 5, (A) and (B) show modes of Z-Lys binding to PylRS(c270) and PylRS(c270) (Y306A) active sites; and (C) shows results obtained from analysis of aminoacylation reaction of Z-Lys with various types of PylRS mutants.
Figure 5B:
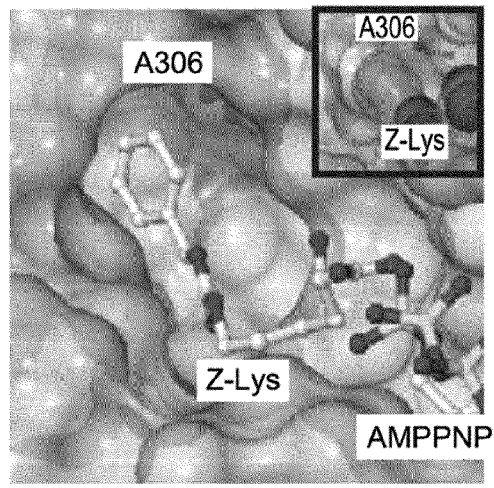
Figure 5C:
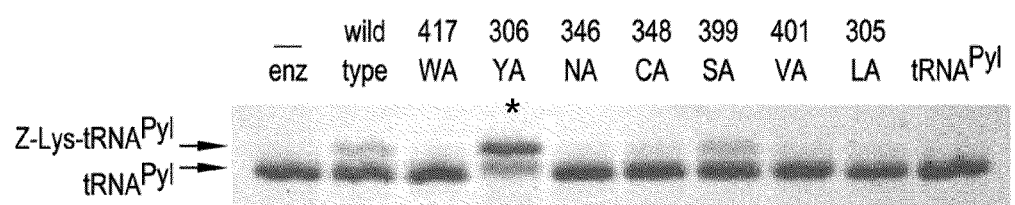

The aminoacylation activity of the PylRS mutants produced as mentioned above were determined using Boc-Lys as a substrate, resulting in that the catalytic activities of the 5 mutants in which alanine was substituted correspondingly for leucine at position 305, tyrosine at position 306, asparagine at position 346, valine at position 401 and tryptophan at position 417 were decreased drastically. Intriguingly, it was found that one PylRS(c270) mutant (Y306A) esterified tRNA$^{Pyl}$ with Z-Lys much more efficiently than the wild-type PylRS (see FIG. 5C). It is considered that this mutation having the substitution of tyrosine at position 306 by alanine generates a cavity suitable to accommodate the benzyloxycarbonyl (Z) group at substrate-binding site of PylRS (FIGS. 5A and 5B).

[Selection of the Boc-Lys-tRNA Synthetase]

From the results of aminoacylation assay in vitro, it was found that although the wild-type PylRS aminoacylated lysine derivatives such as Boc-Lys, these derivatives could not efficiently be incorporated into a protein in *E. coli* cells. Accordingly, the PylRS mutant (Y384F) capable of incorporating Boc-Lys into a protein in vivo efficiently was screened by the following method.

The full length PylRS gene was expressed under the control of *E. coli* TyrRS promoter and terminator in plasmid pTK2-1. This plasmid pTK2-1 is a derivative of plasmid pACYC184 and expresses one copy of the tRNA$^{Pyl}$ gene under the control of the kanamycin resistant gene and the *E. coli* lpp promoter. The PylRS gene was mutagenized randomly at a ratio of three to seven mutations per kb using the GeneMorph PCR mutagenesis kit (Stratagene), and was ligated with the original plasmid pTK2-1 to generate a PylRS library. The ligated vectors were transformed into DH10B competent cells to yield a library of 6×10$^7$ colony forming units. The tRNA$^{Pyl}$ gene was also expressed in *E. coli* DH10B cells under the control of the lpp promoter and the rrnC terminator in plasmid pTK2-1. The PylRS mutant library was first subjected to a positive selection based on suppression of an amber stop codon located at a nonessential position in the chloramphenicol acetyltransferase (CAT) gene. The cells transformed with the PylRS mutant library and the wild-type tRNA$^{Pyl}$ gene were grown in media containing 1 mM Boc-Lys, and cells capable of surviving in the presence of various concentrations of chloramphenicol were screened. Then the surviving cells were grown in the presence of chloramphenicol and the absence of Boc-Lys. In the absence of Boc-Lys, the cells expressing selected PylRS mutants survived merely at the concentration of less than 25 μg/ml of chloramphenicol, whereas in the presence of Boc-Lys, they survived at the concentration of 150 μg/ml of chloramphenicol. Comparing with the CAT resistance of *E. coli* in the absence of PylRS (<13 μg/ml), these results demonstrate that the selected PylRS mutant (Y384F) aminoacylates Boc-Lys, and further aminoacylates any natural amino acids to some degree.

[Lysine Derivative-dependent Amber Suppression in *E. coli* cells.]

Figure 6:
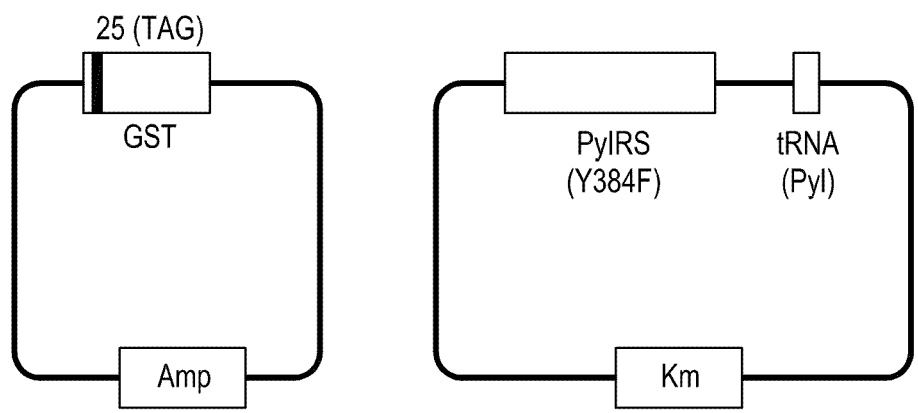
FIG. 6 shows outline of amber suppression system using PylRS and tRNA$^{Pyl}$.
Figure 7:
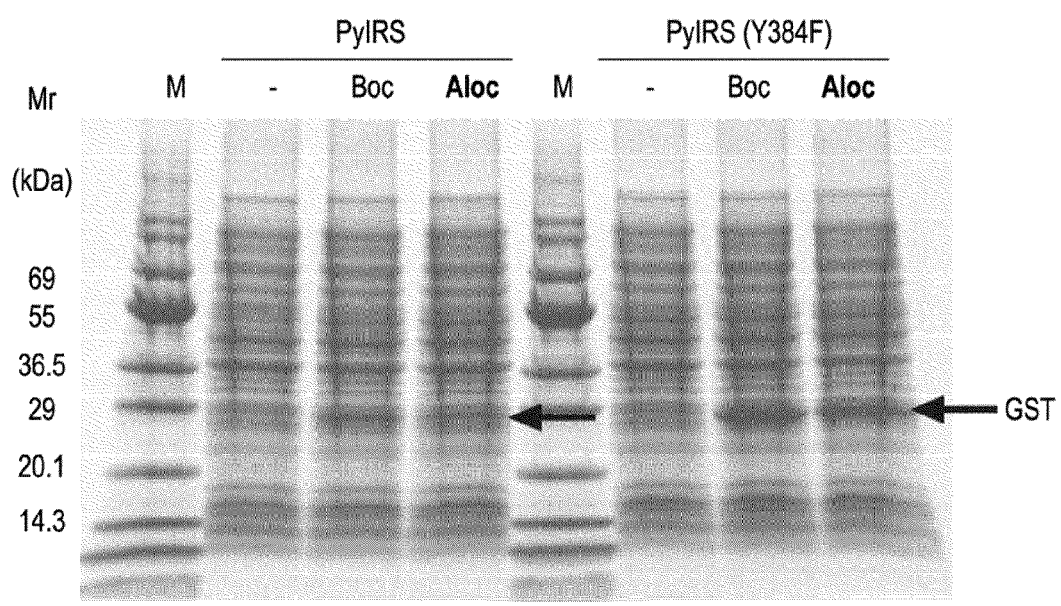
FIG. 7 shows results obtained from SDS-PAGE analysis of proteins which were synthesized by Boc-Lys and Aloc-Lys dependent amber suppression in *E. coli*.
Figure 8:
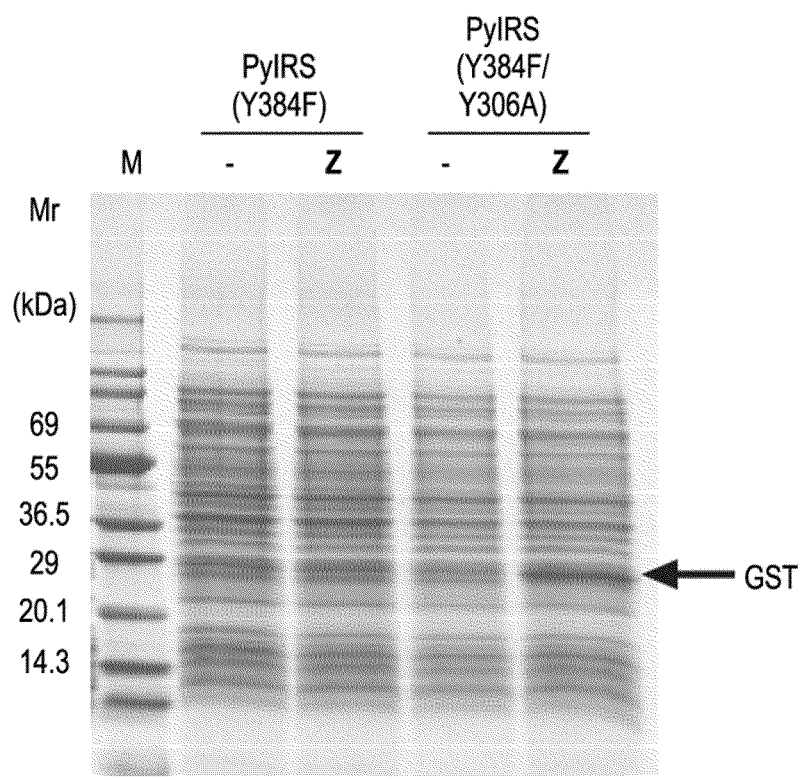
FIG. 8 shows results obtained from SDS-PAGE analysis of proteins which were synthesized by Z-Lys dependent amber suppression in *E. coli*.
Figure 9:
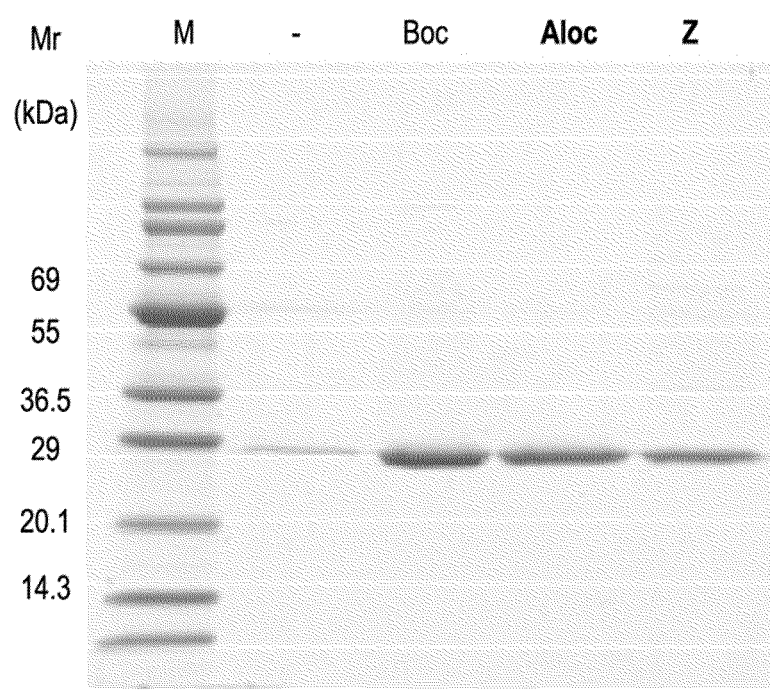
FIG. 9 shows results obtained from analysis of purified GST proteins which were synthesized by amber suppression in *E. coli*.
Figure 10:
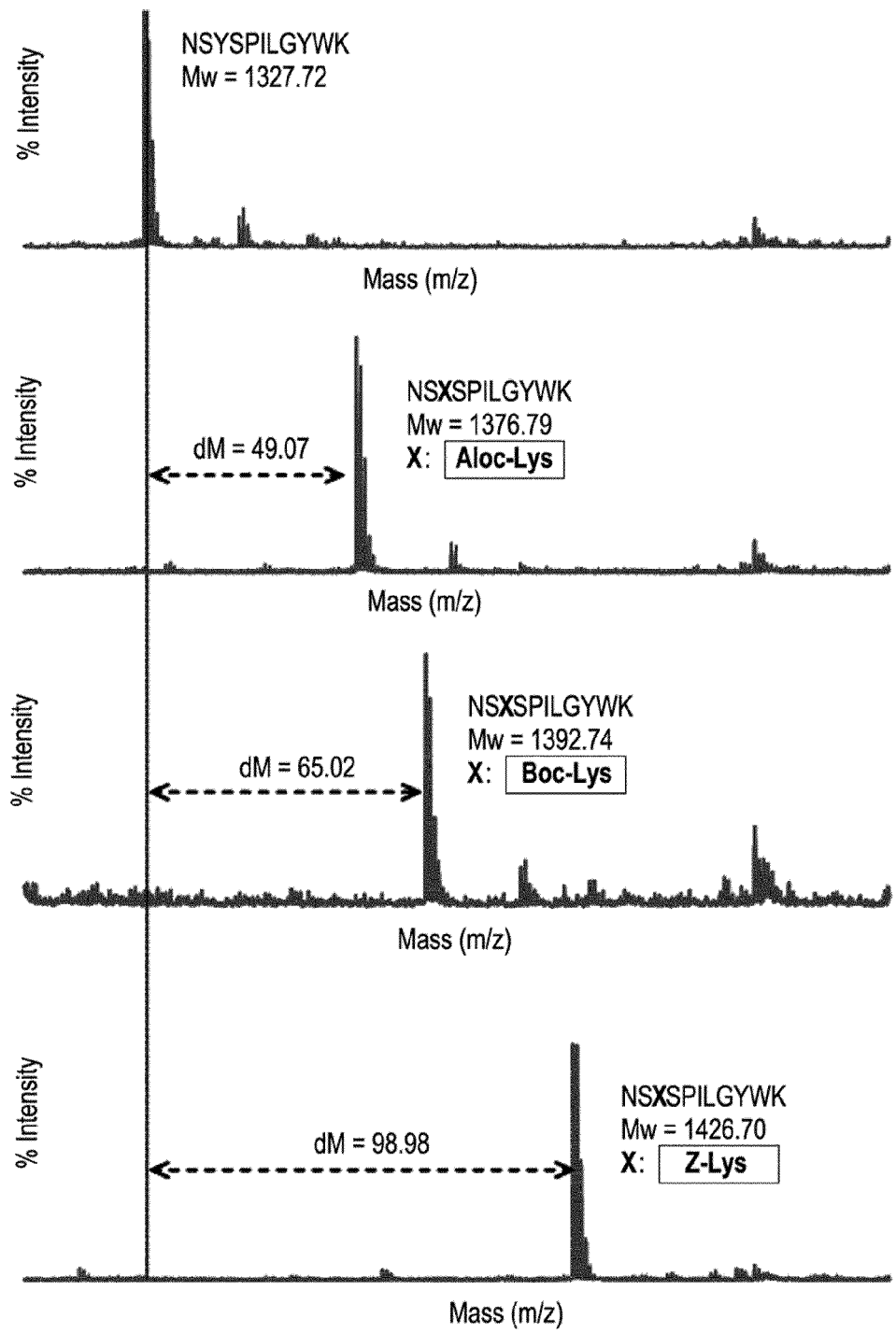
FIG. 10 shows results obtained from analysis by MALDI-TOF mass spectrometry of purified GST proteins (SEQ ID NOS: 17 and 18) which were subjected to in-gel trypsin digestion.

In order to confirm whether amber suppression (amber mutation suppression) occurs in *E. coli* cells, the glutathione S-transferase (GST) gene whose tyrosine codon at the 25th from N terminus was mutated to the amber codon (TAG) was cloned into a pET system plasmid. On the other hand, the wild-type and a variety of mutant PylRS genes, as well as tRNA$^{Pyl}$ genes were cloned into a pACYX system plasmid (see FIG. 6). These two expression vectors were transformed to *E. coli* BL21 (DE3) to statically culture overnight on LB agar medium including kanamycin and ampicillin. Growing colonies were inoculated into LB liquid medium including kanamycin and ampicillin in the presence or absence of lysine derivative, and cultured at ca. 37 degrees Celsius, followed by addition of IPTG such that its final concentration was equivalent to 1 mM when the absorbance of the medium reached to 0.6. Incubation was conducted overnight to induce expression before *E. coli* cells were harvested to detect expressed GST using SDS-PAGE. As a result, it was observed that 28-kDa GST protein was expressed in a case where the mutant PylRS (Y384F) and tRNA$^{Pyl}$ were expressed in the presence of 4 mM of Boc-Lys and in a case where they were expressed in the presence of 4 mM of Aloc-Lys (see FIG. 7). It was also observed that the full length GST protein was produced in a case where double mutant PylRS (Y384F/Y306A) and tRNA$^{Pyl}$ were expressed in the presence of 5 mM Z-Lys (see FIG. 8). *E. coli* cells recovered from 10 ml of the culture medium were supplied with 1 ml of buffer A (potassium phosphate (pH 7.4), 0.15M of NaCl and 10 mM of b-mercaptoethanol) to be subjected to sonication and centrifugation. The resulting supernatant was supplied with 200 ml of glutathione affinity column (GSTrap, Amersham Biosciences Inc.), and stirred at ca. 4 degrees Celsius for 1 h, followed by washing 3 times with buffer A to elute GST protein with buffer A containing 20 mM of glutathione. The thus purified GST protein was yielded 1 to 2 mg of proteins per liter of medium (see FIG. 9). The purified GST protein was degraded with trypsin to analyze with MALDI-TOF mass spectrometry. Detection peaks corresponding to peptides NSXSPI-GYWK (X represents Boc-Lys, Aloc-Lys or Z-Lys) (SEQ ID NO: 18) which were generated with trypsin digestion were m/z=1392.74, 1376.79 and 1426.70 Da, which agreed well with the theoretical values, and were by 65.02, 49.07 and 98.98 Da, respectively, greater than those of the wild-type tryptic peptide NSYSPILGYWK (SEQ ID NO: 17) (m/z=1327.72 Da) (see FIG. 10). The sequence information from the mass spectrums represented in FIG. 10 demonstrates that these non-natural amino acids were site-specifically incorporated into a GST protein.

[Docking Model of PylRS(c270) with tRNA]

Figure 11A:
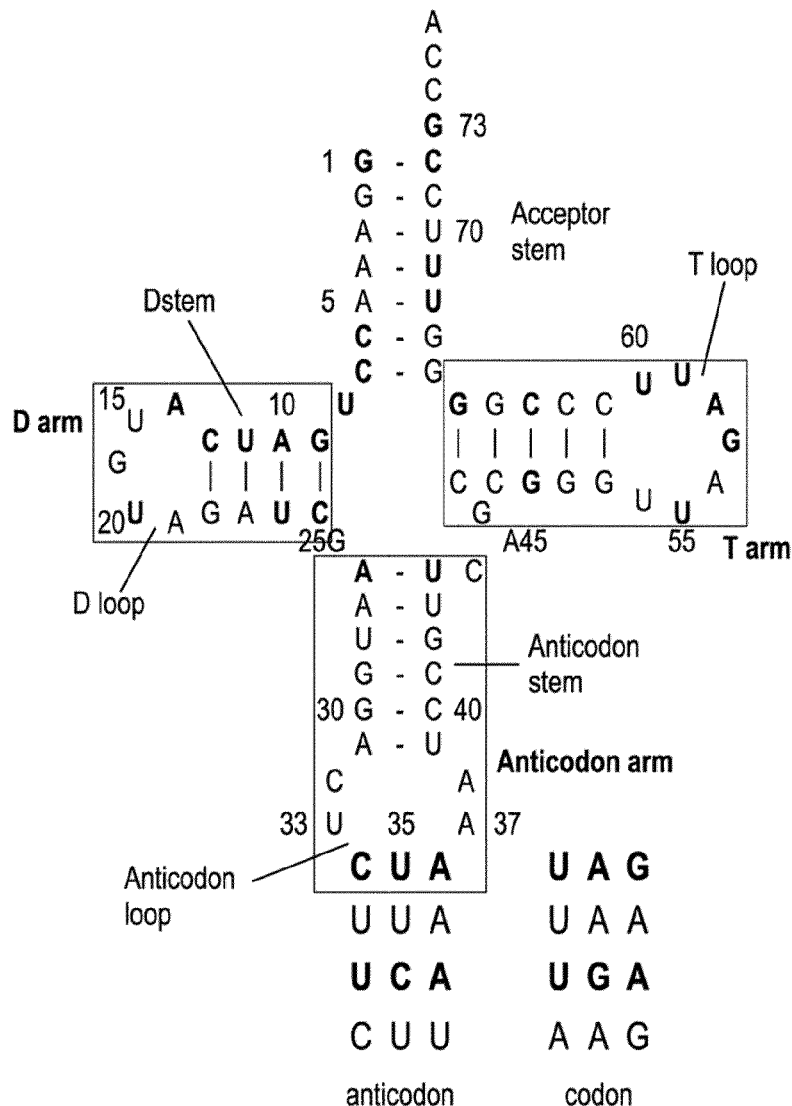
FIG. 11A shows putative secondary structure of *M. mazei* tRNA$^{Pyl}$ (SEQ ID NO: 3).
Figure 11B:
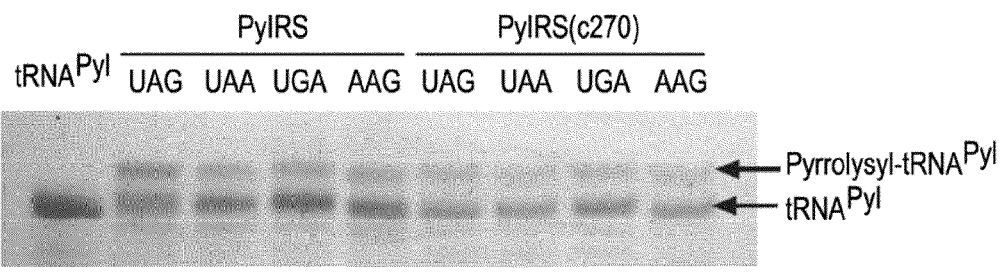
FIG. 11B shows results obtained from research of aminoacylation activity for a variety of nonsense codons.
Figure 12A:
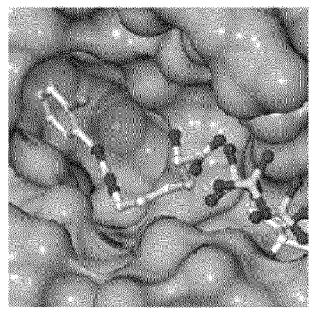
FIG. 12 shows schematic views of chemical structures of a variety of $N^\epsilon$-benzyloxycarbonyl-lysine derivatives and their binding modes with PylRS (Y306A).
Figure 12A:
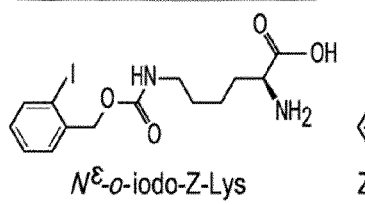
Figure 12B:
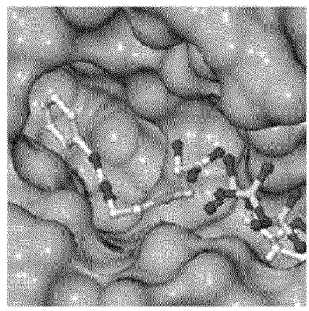
Figure 12B:
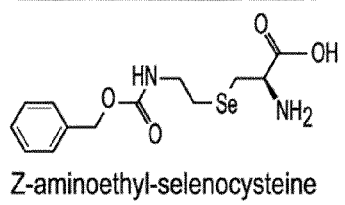
Figure 12C:
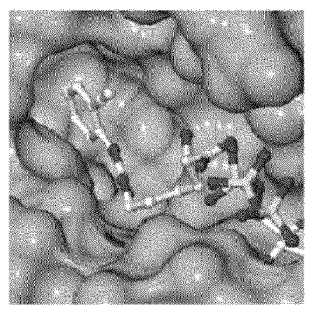
Figure 12C:
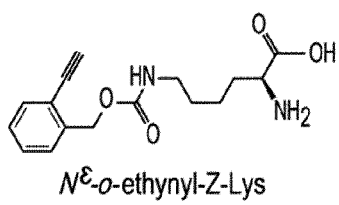
Figure 12D:
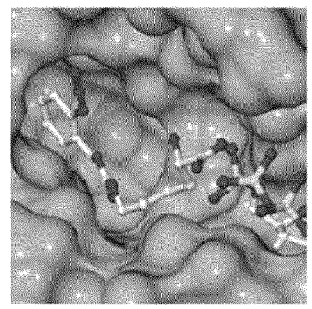
Figure 12D:
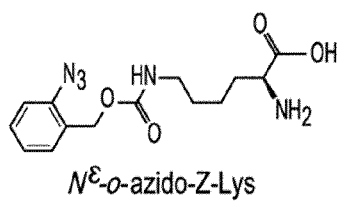
Figure 12E:
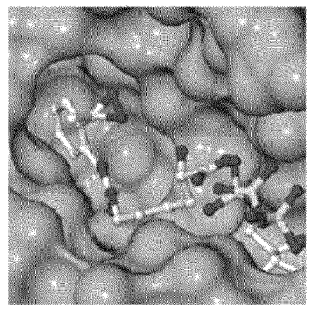
Figure 12E:
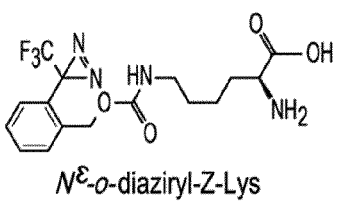

It is notable that the PylRS(c270) maintains the aminoacylation activity of tRNA (see FIG. 1C). This finding indicates that tRNA$^{Pyl}$ may bind to the PylRS of which N-terminal domain is deleted. The catalytic activity site of the PylRS (c270) was superposed onto the tertiary structure of the *E. coli* aspartic acid-tRNA synthetase complexed with tRNA$^{Asp}$ to make a binding model in which tRNA$^{Asp}$ was replaced with yeast tRNA$^{Phe}$. According to this model, the PylRS (c270) contacts with the acceptor stem and the D arm of tRNA. The α1 and α2 helices were adjacent to the D arm of one tRNA protomer. No interaction of PylRS (c270) with the T arm and the anticodon arm was observed. The structure of tRNA$^{Pyl}$ has features significantly different from those of normal tRNA$^{Phe}$, for example, a small D loop consisting only of 5 bases, as shown in FIG. 11A. The full length PylRS of *M. mazei* may also contact with the T arm of tRNA$^{Pyl}$, since the N-terminal helix of the PylRS(c270) protrudes toward the T arm. In addition, mutants in which anticodon sequences of tRNA$^{Pyl}$ were changed to different sequences were produced, none of which affected the enzymatic activity of PylRS. Thus, it has been found that PylRS does not interact with the anticodon loop of tRNA and requires almost no anticodon recognition (see FIG. 11B).

EXAMPLE 2

[Screening of Z-Lys Specific PylRS Mutant]

On the basis of the conformational structure of PylRS (c270) complexed with Boc-Lys and AMPPNP, Z-Lys-specific mutant PylRS was screened by the following method. Of the conformational structure of this complex, the amino acid residue of PylRS localized at position adjacent to the side chain of Boc-Lys was selected to perform saturation mutagenesis. For recognizing the large Z-Lys group, the terminal portion in the amino acid recognition pocket of PylRS must enlarge and widen. In the complex structure of PylRS and Boc-Lys, Tyr306, Leu309, Cys348 and Trp417 constitute the terminal portion of the pocket. However, since the substitution of Trp417 of PylRS by a different amino acid causes loss of the enzymatic activity, a library of mutant enzymes in which codons of the other 3 amino acid residues were replaced with NNK (wherein N represents any of 4 kinds of bases and K represents G or T) was produced (containing 2.3×10$^6$ of independent transformants).

Concretely, the R61K, G131E and Y384F mutant PylRS genes with increased aminoacylation activity against Boc-Lys were cloned under control of glnS promoter in the plasmid pBRQ1 comprising pBR322 replication origin and kanamycin resistant gene. DNA fragments of these PylRS genes whose codon sequences at positions 306, 309 and 348 were randomly replaced with NNK (wherein N represents any of 4 kinds of bases and K represents G or T) were synthesized and amplified by PCR. These fragments were constructed by overlap PCR method to insert into a region downstream of glnS promoter in plasmid pBRQ1. These plasmids were introduced into *E. coli* DH10B carrying a plasmid which contains tRNA$^{pyl}$ gene under control of CAT gene (AM112) having amber mutation and lpp promoter. As positive selection, the resulting transformant was selected on LB plate containing 50 ug/ml of chloramphenicol and 1 mM of Z-Lys, and plasmid DNA was extracted and purified with agarose gel electrophoresis. Subsequently, the resulting plasmid DNA was introduced into *E. coli* DH10B carrying a pACYC184-derived plasmid comprising DNA which had amber codons at positions 2, 44 and 65 in coding region of the barnase gene, which was a bacterial toxin, and were controlled by araC promoter. As negative selection, these cells were incubated on LB plates containing 0.02% arabinose. The positive selection was repeated 3 times and the negative selection was repeated twice.

Figure 13:
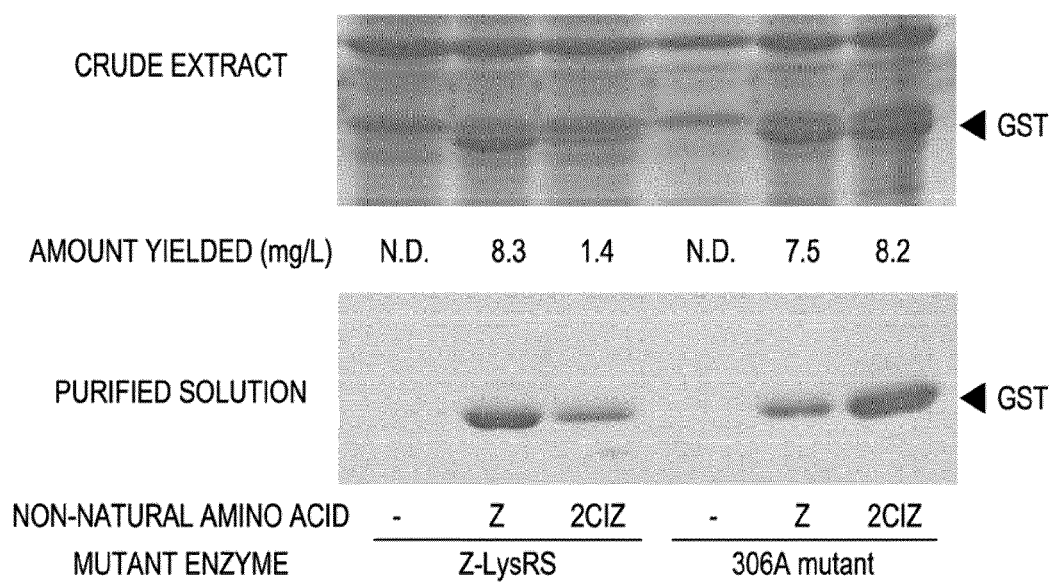
FIG. 13 shows results obtained from SDS-PAGE analysis of GST having amber codon which is expressed in *E. coli* using mutant enzyme having high Z-Lys specificity.

As a result, finally 5 mutants were obtained by the positive selection using 75 µg/ml of chloramphenicol. It was observed that of these 5 mutants, a cell which had an enzyme (hereinafter referred to as Z-LysRS) having double amino acid substitution of L309A and C348V expressed amber-suppressed GST most abundantly (6.9 mg/L medium in M9 GMML medium containing 1 mM of Z-Lys) but showed little expression under the condition of non addition of Z-Lys (see FIG. 13). FIG. 13 shows results obtained from researches of expressions of the full length GST amber-suppressed such that the mutant PylRS (Y306A) obtained in Example 1 and the Z-LysRS obtained in Example 2 were used and 2 kinds of non-natural amino acid Z-Lys(s) or 2-chloro-Z-Lys was added. The upper part and lower part of FIG. 13 show results obtained from 12% SDS-PAGE separation and CBB staining of crude extract from *E. coli* cells and purified GST solution, respectively. The yields in each condition (level (mg) of GST expression per 1 L of M9 GMML medium) were determined according to Bradford method (using BioRad Protein Assay Kit), the results of which were shown in blank between two gels positioned on the upper and lower sides. In FIG. 13, N.D. represents "undetectable".

The purified GST protein was subjected to trypsin digestion and then analyzed with MALDI-TOF mass spectrometry, resulting in that a peptide peak corresponding to NSXSPI-GYWK (SEQ ID NO: 18) (wherein X represents Z-Lys residue, m/z=1426.75 Da) was merely detected and none of peaks of peptides incorporated with other amino acids were detected. Accordingly, it was found that the mutant enzymes Z-LysRS (L309A, C348V) obtained in Example 2 were specific to Z-Lys. Further, it is considered that because, as shown in FIG. 13, Z-LysRS has higher incorporation efficiency of Z-Lys than Y306A whereas the former has lower amount of 2-chloro-derivative as a substrate than the latter, Z-LysRS has higher specificity to Z-Lys than Y306A.

EXAMPLE 3

[Incorporation of N$^\epsilon$-ortho-azide-benzyloxycarbonyl-lysine (AzZLys) into GST Protein in *E. coli* Cells and Modification Reaction Thereof]

Figure 14:
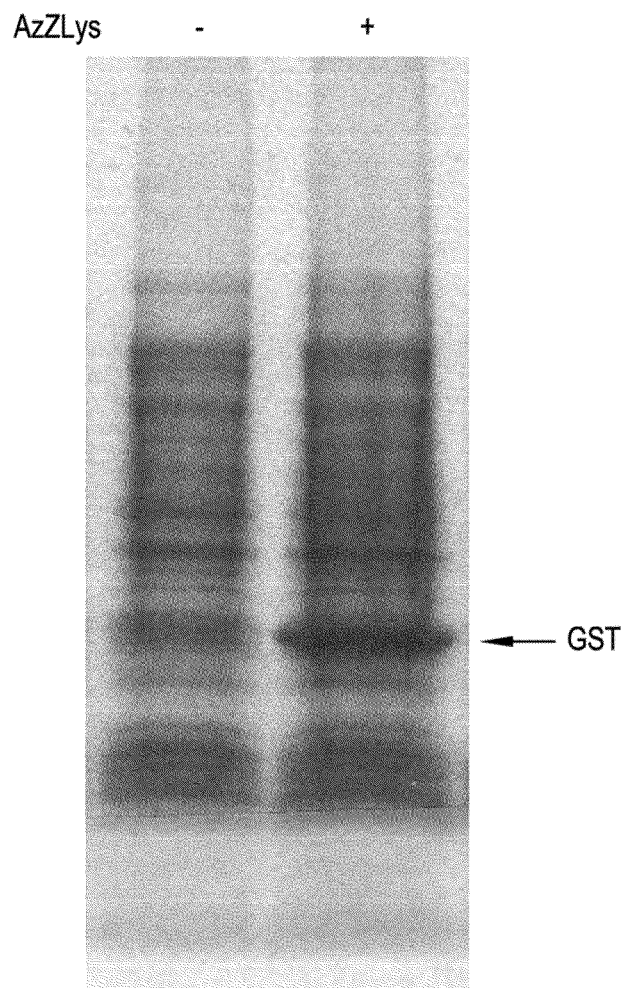
FIG. 14 shows patterns resulting from separating, using SDS-PAGE, crude extracts obtained from *E. coli* in which GST amber gene was expressed and then staining the proteins.

The same plasmid pTK2-1 as Example 1 was used for expressing PylRS mutant with double amino acid substitutions of Y306A and Y384F and tRNA$^{Pyl}$ in *E. coli* cells. Incorporation of a lysine derivative into GST having amber codon at 25th from its N-terminus using this plasmid was performed according to the same method as Example 1. Moreover, specific incorporation of AzZLys [purchased from Shinsei Chemical Company Ltd. (Osaka)] into the amber site in GST using the same plasmid was also performed according to the same method as Example 1. Subsequently, crude extract obtained from *E. coli* cells in which the GST amber gene was expressed was separated with SDS-PAGE and stained. As s result, expression of the full length GST was detected merely in the case of the presence of 1 mM AzZLys (+) (in FIG. 14, the position of the detected band is indicated with an arrow of GST). Furthermore, purification of GST was performed with the same method as Example 1.

Figure 15:
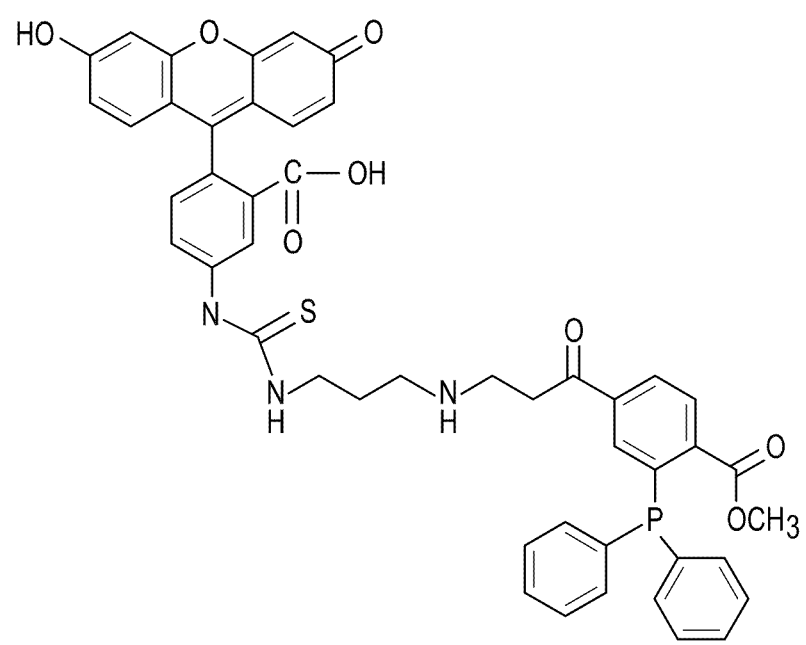
FIG. 15 shows chemical structure of FITC-PP3.
Figure 16:
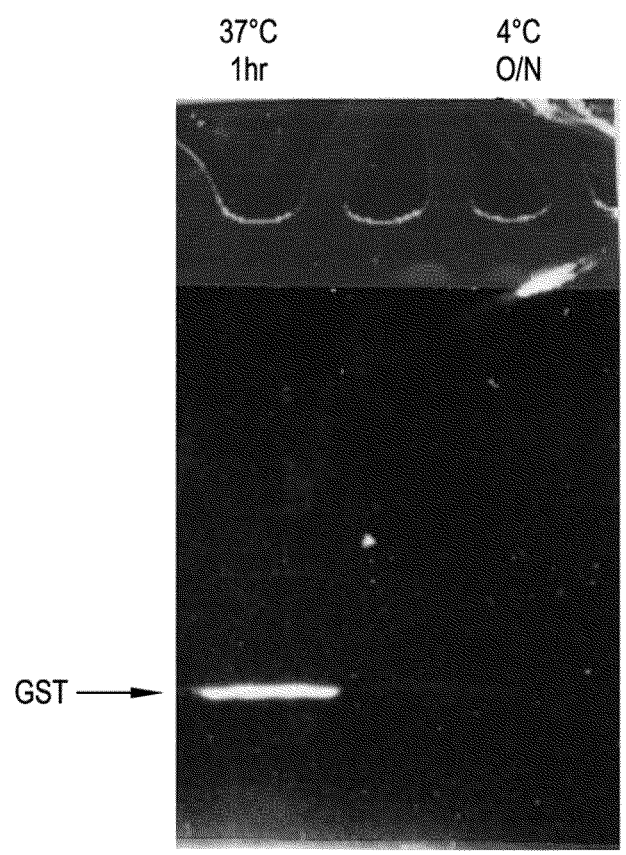
FIG. 16 shows results obtained from SDS-PAGE separation of GSTs which are subjected to 2 types of fluorescence modification reactions and then detection of fluorescence using UV light.

A conjugate of fluorophore and triarylphosphine, and the purified full length GST were linked by Staudinger-Bertozzi reaction. As a conjugate, the conjugate with FITC (hereinafter referred to as FITC-PP3) (purchased from Shinsei Chemical Company Ltd.) was used. FIG. 15 shows the chemical structure of FITC-PP3. Linkage reaction was performed under two types of reactive conditions, i.e., at ca. 37 degrees Celsius for 1 hour (1 hr) and at ca. 4 degrees Celsius overnight (O/N). Subsequently, these GST were separated by SDS-PAGE to detect fluorescence with UV light. As a result, fluorescence-modified GST was detected merely in the case of the reactive condition at ca. 37 degrees Celsius for 1 hour (in FIG. 16, the position of the detected band is indicated with an arrow of GST). As to the Staudinger-Bertozzi reaction, see the above-mentioned Non-Patent Documents 5, 6, etc. This result suggests that it is possible to specifically incorporate AzZLys into a desired site in *E. coli* by using PylRS (Y306A, Y384F) mutant, and that it is possible to incorporate any modification group containing fluorophore into (any) protein [GST protein] by reacting the incorporated AzZLys with phosphine.

[Incorporation of AzZLys into Grb2 Protein in Animal Cell and Fluorescent Modification Reaction]

For expressing PylRS (Y306A, Y384F) mutant and tRNA$^{Pyl}$ in HEK c-18 cell, the system disclosed in the above-mentioned Non-Patent Document 7 was used. Likewise, the mutant gene into which the amber codon was incorporated at the cording region of lac Z gene and GRB2 gene, and the expression system thereof, as disclosed in the above-mentioned Non-Patent Document 7, were used.

Figure 17:
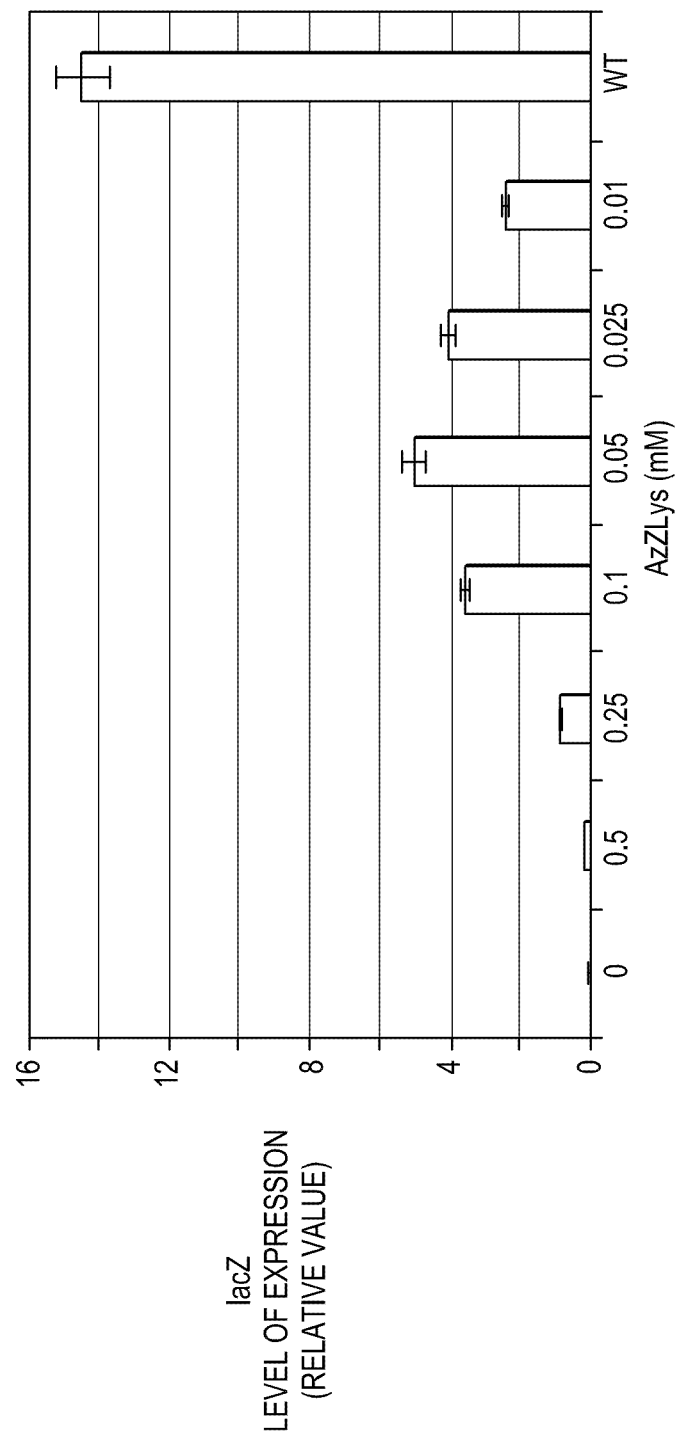
FIG. 17 shows results (or levels) of expression of LacZ protein from lacZ amber gene, which are shown in relative intensity of coloring reaction.

First, in the animal cells, optimal concentration of AzLys for site-specific incorporation of AzLys into the protein was determined. In media containing 0, 0.01, 0.025, 0.05, 0.1, 0.25 and 0.5 mM of AzZLys, LacZ protein was expressed from the lacZ amber gene to determine the level of expression (relative value) of LacZ with coloring reaction by LacZ. As a result, it was found that AzZLys was most efficiently incorporated into the amber site of lacZ in the case of AzZLys being added at the concentration of 0.05 mM (see FIG. 17). In FIG. 17, WT represents the level of expression (relative value) of wild-type (WT) lacZ without any amber codon in the coding region. In comparison to the result of WT, it is apparent that suppression efficiency in the case of the concentration of AzZLys being 0.05 mM is equal to approximately 30% of WT.

Figure 18:
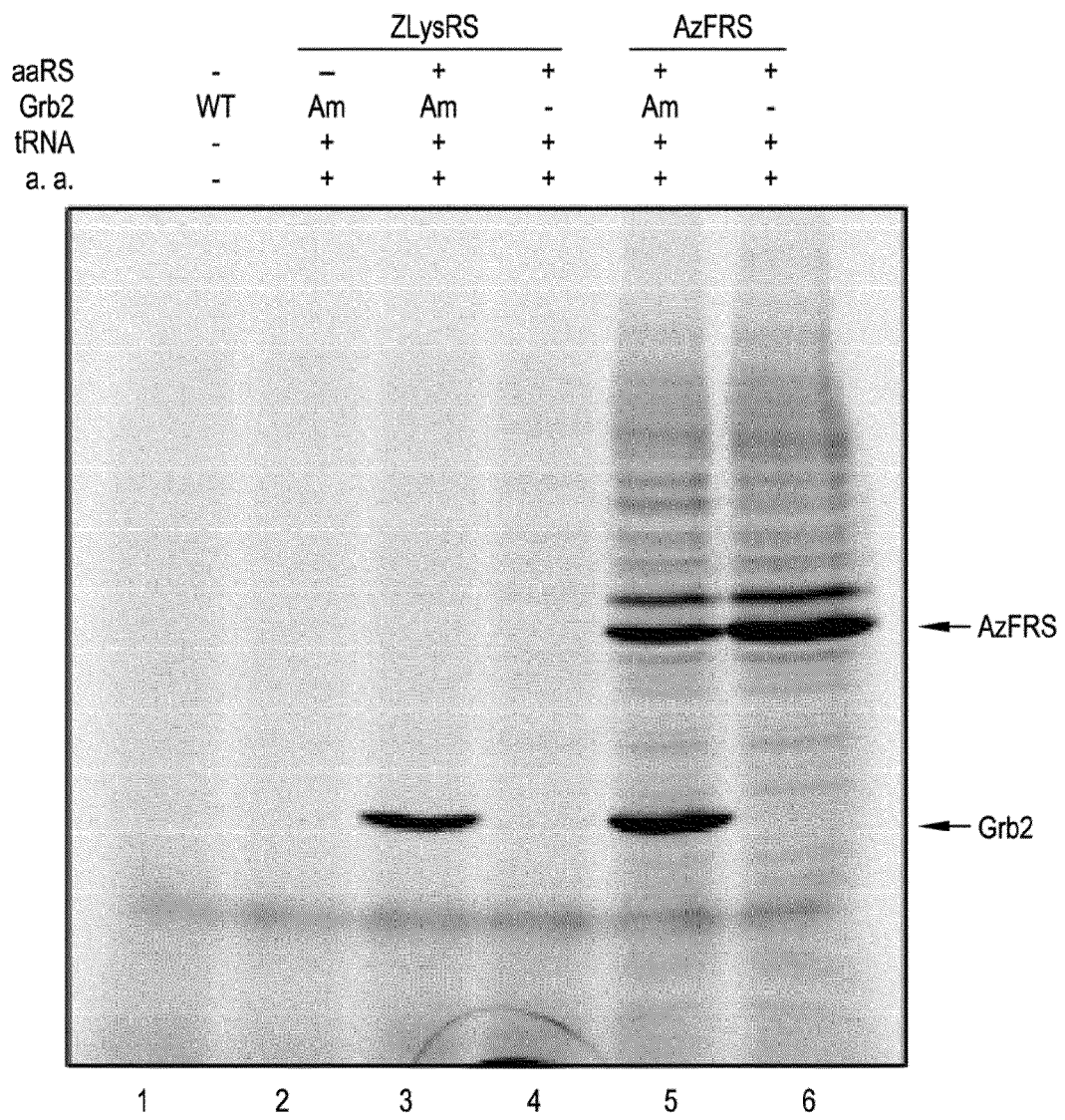
FIG. 18 shows results obtained by performing fluorescence modification reaction in crude extract form animal cells in which Grb2 gene was expressed, and conducting SDS-PAGE separation, and then implementing detection using fluorescence detector.

Fluorescein phosphine-conjugate (FITC-PP3) was added to crude extract from the animal cells in which the GRB2 amber gene was expressed, whereby a Grb2 protein was labeled with fluorescence. Subsequently, separation with SDS-PAGE was performed to detect fluorescence with fluorescence detector (see FIG. 18, at lanes 1 to 3). In FIG. 18, aaRS represents the presence or absence of ZLys expression ("+" represents the presence of the expression), Grb2 represents the presence or absence of GRB2 amber gene expression ("Am" represents the presence of the expression), tRNA represents the presence or absence of tRNA$^{Pyl}$ expression ("+" represents the presence of the expression); and a.a. represents the presence or absence of AzZLys addition ("+" represents addition). As is evident from FIG. 18, a Grb2 protein labeled with fluorescence was detected merely in the case of aaRS (+), Grb2 (Am), tRNA (+) and a.a. (+) (at lane 3)

(wherein the position of the detected band is indicated with an arrow of GST). Incidentally, lane 1 represents the result of WT in the case of the GRB2 gene being used. As is apparent from FIG. 18, no fluorescence labeling bands were detected in lane 1. As a control, para-azide-phenylalanine (hereinafter referred to as AzF) was incorporated into the same site of the Grb2 protein. In order to incorporate AzF into the amber site in animal cells using AzF-specific enzyme (AzFRS), the system disclosed in the above-mentioned Non-Patent Document 8 was used. As is evident from FIG. 18, Grb2 was modified with fluorescence also in the case of AzFRS being used (at lane 5; the position of the detected band is indicated with an arrow of Grb2), and also AzFRS was modified with fluorescence concurrently (at lanes 5 and 6, the positions of the detected bands are indicated with an arrow of AzFRS). This result demonstrates that the distinction between Grb2 and AzFRS cannot be made only by detection of fluorescence, and thus such method is inconvenient.

The above-mentioned results demonstrate that it is possible to specifically incorporate AzZLys into a desired site in animal cells by using PylRS (Y306A, Y384F) mutant and that it is possible to incorporate any arbitrary modification group comprising fluorophore into (any arbitrary) protein [GST protein] by reacting the incorporated AzZLys with phosphine. The above-mentioned results further demonstrate that the system of the present invention used in these Examples is superior in selectivity of modification to conventional systems for incorporating AzF into a protein using AzFRS.

The mutant PylRS of the present invention allows a site-specific incorporation of a non-natural amino acid such as a Z-Lys derivative into a protein, which could not be conducted so far, and thus is useful for synthesizing novel alloproteins. By providing those means, the present invention promotes understanding of complex biological phenomena via analysis of the structure and function of proteins, and thus is industrially applicable in the fields of pharmaceuticals and life science.

It should be noted that changes and modifications of the embodiments or Examples may be done within the entire disclosure (inclusive of the claims) of the present invention and on the basis of the basic technical spirits thereof. Also, it should be noted that a variety of combinations or selections of various elements disclosed may be made within the scope of the claims of the present invention.

In the present invention, there are further possible modes as follows.

mode 1 is as set forth in the first aspect.

mode 2: The mutant pyrrolysyl-tRNA synthetase of Mode 1 may further comprise amino acid substitution of phenylalanine or histidine for tyrosine at position 384.

mode 3: In the mutant pyrrolysyl-tRNA synthetase of Mode 2, the amino acid substitution may comprise double substitution in which alanine is substituted for tyrosine at position 306 and phenylalanine is substituted for tyrosine at position 384.

mode 4: In the mutant pyrrolysyl-tRNA synthetase of Mode 2, the amino acid substitution may comprise double substitution in which alanine is substituted for leucine at position 309 and phenylalanine is substituted for tyrosine at position 384.

mode 5: In the mutant pyrrolysyl-tRNA synthetase of Mode 2, the amino acid substitution may comprise triple substitution in which alanine is substituted for leucine at position 309, valine is substituted for cysteine at position 348, and phenylalanine is substituted for tyrosine at position 384.

mode 6: The mutant pyrrolysyl-tRNA synthetase of any one of Modes 1 to 5, whose amino acid sequence may comprise one or several amino acid deletions, substitutions, or additions at positions other than at positions 306, 309, 348 and 384, and which is capable of aminoacylating $N^\epsilon$-benzyloxycarbonyl-lysine.

mode 7: A mutant pyrrolysyl-tRNA synthetase, obtained from a wild-type pyrrolysyl-tRNA synthetase, which is *Methanosarcina*-derived pyrrolysyl-tRNA synthetase that is a homolog of the amino acid sequence set forth in SEQ ID NO:2, so substituted that when the amino acid sequence of the homolog is aligned with the amino acid sequence set forth in SEQ ID NO:2, the homolog has substitution of alanine for tyrosine corresponding to position 306 of the amino acid sequence set forth in SEQ ID NO:2 and/or substitution of phenylalanine for tyrosine corresponding to position 384 thereof.

mode 8: An isolated DNA encoding the mutant pyrrolysyl-tRNA synthetase of any one of Modes 1 to 7, according to the second aspect.

mode 9: In an expression vector which, when it is introduced into a host cell, is capable of producing the mutant pyrrolysyl-tRNA synthetase of any one of Modes 1 to 7 in host cell, the expression vector may comprise the DNA of Mode 8 which is functionally bound to an expression control sequence in the host cell.

mode 10: *Eubacterium* transformed with the expression vector of Mode 9.

mode 11: *Escherichia coli* transformed with the expression vector of Mode 9.

mode 12: Mammalian culture cell transformed with the expression vector of Mode 9.

mode 13: A method of producing a non-natural amino acid-incorporated protein according to the third aspect.

mode 14: In the method of Mode 13, the aminoacyl-tRNA synthetase may be the mutant pyrrolysyl-tRNA synthetase of any one of Modes 1 to 5.

mode 15: In the method of Mode 13 or 14, the $N^\epsilon$-benzyloxycarbonyl-lysine derivative may be:
$N^\epsilon$-ortho-iodo-benzyloxycarbonyl-lysine;
benzyloxycarbonyl-aminoethyl-selenocysteine;
$N^\epsilon$-ortho-ethinyl-benzyloxycarbonyl-lysine;
$N^\epsilon$-ortho-azide-benzyloxycarbonyl-lysine; or
$N^\epsilon$-ortho-diaziryl-benzyloxycarbonyl-lysine.

mode 16: A kit for synthesizing non-natural amino acid-incorporated protein according to the fourth aspect.

What is claimed is:

1. A mutant pyrrolysyl-tRNA synthetase comprising substitution of at least one amino acid residue selected from tyrosine at position 306, leucine at position 309, and cysteine at position 348, which constitute a pyrrolysine-binding site, and tyrosine at position 384, in the amino acid sequence of the pyrrolysyl-tRNA synthetase set forth in SEQ ID NO:2,
   wherein said substitution of the amino acid residue comprises:
   substitution of alanine for tyrosine at position 306,
   substitution of phenylalanine for tyrosine at position 384,
   double substitution in which alanine is substituted for tyrosine at position 306 and phenylalanine is substituted for tyrosine at position 384, or
   double substitution in which alanine is substituted for leucine at position 309 and valine is substituted for cysteine at position 348,
   wherein said mutant pyrrolysyl-tRNA synthetase aminoacylates a pyrrolysine tRNA with N$^\epsilon$-benzyloxycarbonyl-lysine more efficiently than the wild type pyrrolysyl-tRNA synthetase having the amino acid sequence set forth in SEQ ID NO: 2.

2. The mutant pyrrolysyl-tRNA synthetase of claim 1, whose amino acid sequence further comprises one or several amino acid deletions, substitutions, or additions at positions other than at positions 306, 309, 348 and 384, and which is capable of aminoacylating a tRNA with N$^\epsilon$-benzyloxycarbonyl-lysine.

3. A mutant Methanosarcina pyrrolysyl-tRNA synthetase, obtained from the wild-type pyrrolysyl-tRNA synthetase of SEQ ID NO: 2, wherein said mutant Methanosarcina pyrrolysyl-tRNA synthetase comprises a substitution of phenylalanine for tyrosine at a position corresponding to position 384 in the amino acid sequence set forth in SEQ ID NO: 2, and optionally a substitution of alanine for tyrosine at a position corresponding to position 306 in the amino acid sequence set forth in SEQ ID NO: 2; and the mutant pyrrolysyl-tRNA synthetase aminoacylates a pyrrolysine tRNA with N$\epsilon$-benzyloxycarbonyl-lysine.

4. A kit for synthesizing non-natural amino acid-incorporated protein comprising:
   (a) cell extract;
   (b) a non-natural amino acid that is N$^\epsilon$-benzyloxycarbonyl-lysine;
   (c) the mutant pyrrolysyl-tRNA synthetase of claim 1; and
   (d) a suppressor tRNA capable of binding to N$^\epsilon$-benzyloxycarbonyl-lysine in the presence of said mutant pyrrolysyl-tRNA synthetase
   wherein said mutant pyrrolysine tRNA synthetase aminoacylates a pyrrolysine tRNA with N$^\epsilon$-benzyloxycarbonyl-lysine more efficiently than the wild type pyrrolysyl-tRNA synthetase set forth in SEQ ID NO: 2.

5. A mutant pyrrolysyl-tRNA synthetase comprising an amino acid sequence having at least 90% sequence identity to the amino acid sequence of SEQ ID NO: 2 and comprising substitution of at least one amino acid residue selected from tyrosine at position 306, leucine at position 309, and cysteine at position 348, which constitute a pyrrolysine-binding site, and tyrosine at position 384 in the amino acid sequence of the pyrrolysyl-tRNA synthetase set forth in SEQ ID NO:2, wherein said substitution of the amino acid residue is substitution of alanine for tyrosine at position 306, substitution of phenylalanine for tyrosine at position 384, double substitution in which alanine is substituted for tyrosine at position 306 and phenylalanine is substituted for tyrosine at position 384, or double substitution in which alanine is substituted for leucine at position 309 and valine is substituted for cysteine at position 348, wherein the mutant pyrrolysyl-tRNA synthetase aminoacylates a pyrrolysine tRNA with $N^\epsilon$-benzyloxycarbonyl-lysine more efficiently than the wild type pyrrolysyl-tRNA synthetase having the amino acid sequence set forth in SEQ ID NO:2.

6. The mutant pyrrolysyl-tRNA synthetase of claim 5, wherein the mutant pyrrolysyl-tRNA synthetase has a mutation Y306A.

7. The mutant pyrrolysyl-tRNA synthetase of claim 5, wherein:

the mutant pyrrolysyl-tRNA synthetase has a mutation Y384F; and the mutant pyrrolysyl-tRNA synthetase has activity of aminocylating a tRNA with t-butyloxycarbonyl-lysine.

8. The mutant pyrrolysyl-tRNA synthetase of claim 1, wherein:

the mutant pyrrolysyl-tRNA synthetase has a mutation Y306A and a mutation Y384F; and the mutant pyrrolysyl-tRNA synthetase has activity of aminoacylating a tRNA with t-butoxycarbonyl-lysine, $N^\epsilon$-benzyloxycarbonyl-lysine, allyoxycarbonyl-lysine, or $N^\epsilon$-ortho-azide-benzyloxycarbonyl-lysine.

9. A mutant pyrrolysyl-tRNA synthetase comprising substitution of at least one amino acid residue selected from tyrosine at position 306 and leucine at position 309 in the amino acid sequence of the pyrrolysyl-tRNA synthetase set forth in SEQ ID NO:2, and that is capable of aminoacylating a tRNA with $N^\epsilon$-benzyloxycarbonyl-lysine more efficiently than the wild-type pyrrolysyl-tRNA synthetase having the amino acid sequence of SEQ ID NO:2.

10. The mutant pyrrolysyl-tRNA synthetase of claim 9, having at least one further mutation at position 384 and/or position 348 of SEQ ID NO: 2.

11. The mutant pyrrolysyl-tRNA synthetase of claim 9, wherein the substitution mutation at position 306 is of alanine for tyrosine and the substitution mutation of position 309 is of alanine for leucine.

12. The mutant pyrrolysyl-tRNA synthetase of claim 10, wherein the substitution mutation at position 348 is of valine for cysteine and the substitution mutation at position 384 is of phenylalanine for tyrosine.

13. A mutant pyrrolysyl-tRNA synthetase that is a single or double mutant having one or two substitution mutations selected from the group consisting of:

i) substitution of the amino acid at position 306 of SEQ ID NO: 2;

ii) substitution of the amino acid at position 309 of SEQ ID NO: 2; and iii) substitution of the amino acid at position 306 and of the amino acid at position 309 of SEQ ID NO: 2 ; wherein said substitutions are of glycine or alanine for tyrosine at position 306 and substitution of glycine or alanine for leucine at position 309 and wherein said mutant pyrrolysine tRNA synthetase aminoacylates a pyrrolysine tRNA with $N^\epsilon$-benzyloxycarbonyl-lysine more efficiently than the wild type pyrrolysyl-tRNA synthetase set forth in SEQ ID NO: 2.

14. A mutant pyrrolysyl-tRNA synthetase having two, three or four mutations selected from the group consisting of:

i) substitution of the amino acid at position 306 and substitution of the amino acid at position 348 of SEQ ID NO: 2;

ii) substitution of the amino acid at position 306 and substitution of the amino acid at position 384 of SEQ ID NO: 2;

iii) substitution of the amino acid at position 309 and substitution of the amino acid at position 348 of SEQ ID NO: 2;

iv) substitution of the amino acid at position 309 and substitution of the amino acid at position 384 of SEQ ID NO: 2;

v) substitution of the amino acid at position 306, substitution of the amino acid at position 309 and substitution of the amino acid at position 348 of SEQ ID NO: 2;

vi) substitution of the amino acid at position 306, substitution of the amino acid at position 309 and substitution of the amino acid at position 384 of SEQ ID NO: 2;

vii) substitution of the amino acid at position 306, substitution of the amino acid at position 348 and substitution of the amino acid at position 384 of SEQ ID NO: 2;

viii) substitution of the amino acid at position 309, substitution of the amino acid at position 348 and substitution of the amino acid at position 384 of SEQ ID NO: 2; and ix) substitution of the amino acid at position 306, substitution of the amino acid at position 309, substitution of the amino acid at position 348 and substitution of the amino acid at position 384 of SEQ ID NO: 2;

wherein said substitution is of glycine or alanine for tyrosine at position 306, substitution of glycine or alanine for leucine at position 309, substitution of valine, serine or alanine for cysteine at position 348 and of phenylalanine or histidine for tyrosine at position 384 and wherein said mutant pyrrolysine tRNA synthetase aminoacylates a pyrrolysine tRNA with t-butoxycarbonyl-lysine, $N^\epsilon$-benzyloxycarbonyl-lysine, allyoxycarbonyl-lysine, or $N^\epsilon$-ortho-azide-benzyloxycarbonyl-lysine more efficiently than the wild type pyrrolysyl-tRNA synthetase set forth in SEQ ID NO: 2.

\* \* \* \* \*

SEQUENCE LISTING

<160> NUMBER OF SEQ ID NOS: 18

<210> SEQ ID NO 1
<211> LENGTH: 1365
<212> TYPE: DNA
<213> ORGANISM: Methanosarcina mazei
<220> FEATURE:

<221> NAME/KEY: CDS
<222> LOCATION: (1)..(1365)

<400> SEQUENCE: 1

```
atg gat aaa aaa cca cta aac act ctg ata tct gca acc ggg ctc tgg        48
Met Asp Lys Lys Pro Leu Asn Thr Leu Ile Ser Ala Thr Gly Leu Trp
1               5                   10                  15 atg tcc agg acc gga aca att cat aaa ata aaa cac cac gaa gtc tct        96
Met Ser Arg Thr Gly Thr Ile His Lys Ile Lys His His Glu Val Ser
            20                  25                  30 cga agc aaa atc tat att gaa atg gca tgc gga gac cac ctt gtt gta       144
Arg Ser Lys Ile Tyr Ile Glu Met Ala Cys Gly Asp His Leu Val Val
        35                  40                  45 aac aac tcc agg agc agc agg act gca aga gcg ctc agg cac cac aaa       192
Asn Asn Ser Arg Ser Ser Arg Thr Ala Arg Ala Leu Arg His His Lys
    50                  55                  60 tac agg aag acc tgc aaa cgc tgc agg gtt tcg gat gag gat ctc aat       240
Tyr Arg Lys Thr Cys Lys Arg Cys Arg Val Ser Asp Glu Asp Leu Asn
65                  70                  75                  80 aag ttc ctc aca aag gca aac gaa gac cag aca agc gta aaa gtc aag       288
Lys Phe Leu Thr Lys Ala Asn Glu Asp Gln Thr Ser Val Lys Val Lys
                85                  90                  95 gtc gtt tct gcc cct acc aga acg aaa aag gca atg cca aaa tcc gtt       336
Val Val Ser Ala Pro Thr Arg Thr Lys Lys Ala Met Pro Lys Ser Val
            100                 105                 110 gcg aga gcc ccg aaa cct ctt gag aat aca gaa gcg gca cag gct caa       384
Ala Arg Ala Pro Lys Pro Leu Glu Asn Thr Glu Ala Ala Gln Ala Gln
        115                 120                 125 cct tct gga tct aaa ttt tca cct gcg ata ccg gtt tcc acc caa gag       432
Pro Ser Gly Ser Lys Phe Ser Pro Ala Ile Pro Val Ser Thr Gln Glu
    130                 135                 140 tca gtt tct gtc ccg gca tct gtt tca aca tca ata tca agc att tct       480
Ser Val Ser Val Pro Ala Ser Val Ser Thr Ser Ile Ser Ser Ile Ser
145                 150                 155                 160 aca gga gca act gca tcc gca ctg gta aaa ggg aat acg aac ccc att       528
Thr Gly Ala Thr Ala Ser Ala Leu Val Lys Gly Asn Thr Asn Pro Ile
                165                 170                 175 aca tcc atg tct gcc cct gtt cag gca agt gcc ccc gca ctt acg aag       576
Thr Ser Met Ser Ala Pro Val Gln Ala Ser Ala Pro Ala Leu Thr Lys
            180                 185                 190 agc cag act gac agg ctt gaa gtc ctg tta aac cca aaa gat gag att       624
Ser Gln Thr Asp Arg Leu Glu Val Leu Leu Asn Pro Lys Asp Glu Ile
        195                 200                 205 tcc ctg aat tcc ggc aag cct ttc agg gag ctt gag tcc gaa ttg ctc       672
Ser Leu Asn Ser Gly Lys Pro Phe Arg Glu Leu Glu Ser Glu Leu Leu
    210                 215                 220 tct cgc aga aaa aaa gac ctg cag cag atc tac gcg gaa gaa agg gag       720
Ser Arg Arg Lys Lys Asp Leu Gln Gln Ile Tyr Ala Glu Glu Arg Glu
225                 230                 235                 240 aat tat ctg ggg aaa ctc gag cgt gaa att acc agg ttc ttt gtg gac       768
Asn Tyr Leu Gly Lys Leu Glu Arg Glu Ile Thr Arg Phe Phe Val Asp
                245                 250                 255 agg ggt ttt ctg gaa ata aaa tcc ccg atc ctg atc cct ctt gag tat       816
Arg Gly Phe Leu Glu Ile Lys Ser Pro Ile Leu Ile Pro Leu Glu Tyr
            260                 265                 270 atc gaa agg atg ggc att gat aat gat acc gaa ctt tca aaa cag atc       864
Ile Glu Arg Met Gly Ile Asp Asn Asp Thr Glu Leu Ser Lys Gln Ile
        275                 280                 285 ttc agg gtt gac aag aac ttc tgc ctg aga ccc atg ctt gct cca aac       912
Phe Arg Val Asp Lys Asn Phe Cys Leu Arg Pro Met Leu Ala Pro Asn
    290                 295                 300
```

```
ctt tac aac tac ctg cgc aag ctt gac agg gcc ctg cct gat cca ata      960
Leu Tyr Asn Tyr Leu Arg Lys Leu Asp Arg Ala Leu Pro Asp Pro Ile
305                 310                 315                 320 aaa att ttt gaa ata ggc cca tgc tac aga aaa gag tcc gac ggc aaa     1008
Lys Ile Phe Glu Ile Gly Pro Cys Tyr Arg Lys Glu Ser Asp Gly Lys
                325                 330                 335 gaa cac ctc gaa gag ttt acc atg ctg aac ttc tgc cag atg gga tcg     1056
Glu His Leu Glu Glu Phe Thr Met Leu Asn Phe Cys Gln Met Gly Ser
            340                 345                 350 gga tgc aca cgg gaa aat ctt gaa agc ata att acg gac ttc ctg aac     1104
Gly Cys Thr Arg Glu Asn Leu Glu Ser Ile Ile Thr Asp Phe Leu Asn
        355                 360                 365 cac ctg gga att gat ttc aag atc gta ggc gat tcc tgc atg gtc tat     1152
His Leu Gly Ile Asp Phe Lys Ile Val Gly Asp Ser Cys Met Val Tyr
    370                 375                 380 ggg gat acc ctt gat gta atg cac gga gac ctg gaa ctt tcc tct gca     1200
Gly Asp Thr Leu Asp Val Met His Gly Asp Leu Glu Leu Ser Ser Ala
385                 390                 395                 400 gta gtc gga ccc ata ccg ctt gac cgg gaa tgg ggt att gat aaa ccc     1248
Val Val Gly Pro Ile Pro Leu Asp Arg Glu Trp Gly Ile Asp Lys Pro
                405                 410                 415 tgg ata ggg gca ggt ttc ggg ctc gaa cgc ctt cta aag gtt aaa cac     1296
Trp Ile Gly Ala Gly Phe Gly Leu Glu Arg Leu Leu Lys Val Lys His
            420                 425                 430 gac ttt aaa aat atc aag aga gct gca agg tcc ggg tct tac tat aac     1344
Asp Phe Lys Asn Ile Lys Arg Ala Ala Arg Ser Gly Ser Tyr Tyr Asn
        435                 440                 445 ggg att tct acc aac ctg taa                                         1365
Gly Ile Ser Thr Asn Leu
    450

<210> SEQ ID NO 2
<211> LENGTH: 454
<212> TYPE: PRT
<213> ORGANISM: Methanosarcina mazei

<400> SEQUENCE: 2

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
```

```
                165                 170                 175
Thr Ser Met Ser Ala Pro Val Gln Ala Ser Pro Ala Leu Thr Lys
            180                 185                 190

Ser Gln Thr Asp Arg Leu Glu Val Leu Leu Asn Pro Lys Asp Glu Ile
            195                 200                 205

Ser Leu Asn Ser Gly Lys Pro Phe Arg Glu Leu Glu Ser Glu Leu Leu
        210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
        290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Tyr
        370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Gly Ser Tyr Tyr Asn
            435                 440                 445

Gly Ile Ser Thr Asn Leu
        450

<210> SEQ ID NO 3
<211> LENGTH: 72
<212> TYPE: RNA
<213> ORGANISM: Methanosarcina mazeii

<400> SEQUENCE: 3
ggaaaccuga ucauguagau cgaauggacu cuaaauccgu ucagccgggu uagauucccg      60
ggguuuccgc ca                                                         72

<210> SEQ ID NO 4
<211> LENGTH: 20
<212> TYPE: PRT
<213> ORGANISM: Artificial Sequence
<220> FEATURE:
<223> OTHER INFORMATION: synthetic - His-tag

<400> SEQUENCE: 4

Met Gly Ser Ser His His His His His His Ser Ser Gly Leu Val Pro
1               5                   10                  15
```

```
Arg Gly Ser His
           20

<210> SEQ ID NO 5
<211> LENGTH: 35
<212> TYPE: DNA
<213> ORGANISM: Artificial Sequence
<220> FEATURE:
<223> OTHER INFORMATION: N-terminal primer of full-length PylRS

<400> SEQUENCE: 5
aggggtaacc atatggataa aaaccacta aacac                              35

<210> SEQ ID NO 6
<211> LENGTH: 40
<212> TYPE: DNA
<213> ORGANISM: Artificial Sequence
<220> FEATURE:
<223> OTHER INFORMATION: synthetic - C-terminal primer of full-length
      PylRS

<400> SEQUENCE: 6
acatggtcca gagctcttac aggttggtag aaatcccgtt                        40

<210> SEQ ID NO 7
<211> LENGTH: 12
<212> TYPE: DNA
<213> ORGANISM: Unknown
<220> FEATURE:
<223> OTHER INFORMATION: synthetic - Consensus sequence of Box A
<220> FEATURE:
<221> NAME/KEY: misc_feature
<222> LOCATION: (5)..(6)
<223> OTHER INFORMATION: n stands for
<220> FEATURE:
<221> NAME/KEY: misc_feature
<222> LOCATION: (10)..(10)
<223> OTHER INFORMATION: n stands for any base

<400> SEQUENCE: 7
trgcnnagyn gg                                                      12

<210> SEQ ID NO 8
<211> LENGTH: 11
<212> TYPE: DNA
<213> ORGANISM: Unknown
<220> FEATURE:
<223> OTHER INFORMATION: synthetic - Consensus sequence of Box B
<220> FEATURE:
<221> NAME/KEY: misc_feature
<222> LOCATION: (8)..(8)
<223> OTHER INFORMATION: n stands for any base

<400> SEQUENCE: 8
ggttcgantc c                                                       11

<210> SEQ ID NO 9
<211> LENGTH: 270
<212> TYPE: PRT
<213> ORGANISM: M. mazei

<400> SEQUENCE: 9

Ala Ser Ala Pro Ala Leu Thr Lys Ser Gln Thr Asp Arg Leu Glu Val
1               5                   10                  15

Leu Leu Asn Pro Lys Asp Glu Ile Ser Leu Asn Ser Gly Lys Pro Phe
            20                  25                  30

Arg Glu Leu Glu Ser Glu Leu Leu Ser Arg Arg Lys Lys Asp Leu Gln
```

```
            35                  40                  45
Gln Ile Tyr Ala Glu Glu Arg Glu Asn Tyr Leu Gly Lys Leu Glu Arg
 50                  55                  60

Glu Ile Thr Arg Phe Phe Val Asp Arg Gly Phe Leu Glu Ile Lys Ser
 65                  70                  75                  80

Pro Ile Leu Ile Pro Leu Glu Tyr Ile Glu Arg Met Gly Ile Asp Asn
                 85                  90                  95

Asp Thr Glu Leu Ser Lys Gln Ile Phe Arg Val Asp Lys Asn Phe Cys
                100                 105                 110

Leu Arg Pro Met Leu Ala Pro Asn Leu Tyr Asn Tyr Leu Arg Lys Leu
                115                 120                 125

Asp Arg Ala Leu Pro Asp Pro Ile Lys Ile Phe Glu Ile Gly Pro Cys
130                 135                 140

Tyr Arg Lys Glu Ser Asp Gly Lys Glu His Leu Glu Glu Phe Thr Met
145                 150                 155                 160

Leu Asn Phe Cys Gln Met Gly Ser Gly Cys Thr Arg Glu Asn Leu Glu
                165                 170                 175

Ser Ile Ile Thr Asp Phe Leu Asn His Leu Gly Ile Asp Phe Lys Ile
                180                 185                 190

Val Gly Asp Ser Cys Met Val Tyr Gly Asp Thr Leu Asp Val Met His
                195                 200                 205

Gly Asp Leu Glu Leu Ser Ser Ala Val Val Gly Pro Ile Pro Leu Asp
            210                 215                 220

Arg Glu Trp Gly Ile Asp Lys Pro Trp Ile Gly Ala Gly Phe Gly Leu
225                 230                 235                 240

Glu Arg Leu Leu Lys Val Lys His Asp Phe Lys Asn Ile Lys Arg Ala
                245                 250                 255

Ala Arg Ser Glu Ser Tyr Tyr Asn Gly Ile Ser Thr Asn Leu
                260                 265                 270

<210> SEQ ID NO 10
<211> LENGTH: 272
<212> TYPE: PRT
<213> ORGANISM: Methanosarcina barkeri

<400> SEQUENCE: 10

Ala Ser Ala Pro Ala Pro Ser Leu Thr Arg Ser Gln Leu Asp Arg Val
 1               5                  10                  15

Glu Ala Leu Leu Ser Pro Glu Asp Lys Ile Ser Leu Asn Met Ala Lys
                 20                  25                  30

Pro Phe Arg Glu Leu Glu Pro Glu Leu Val Thr Arg Arg Lys Asn Asp
                 35                  40                  45

Phe Gln Arg Leu Tyr Thr Asn Asp Arg Glu Asp Tyr Leu Gly Lys Leu
 50                  55                  60

Glu Arg Asp Ile Thr Lys Phe Phe Val Asp Arg Gly Phe Leu Glu Ile
 65                  70                  75                  80

Lys Ser Pro Ile Leu Ile Pro Ala Glu Tyr Val Glu Arg Met Gly Ile
                 85                  90                  95

Asn Asn Asp Thr Glu Leu Ser Lys Gln Ile Phe Arg Val Asp Lys Asn
                100                 105                 110

Leu Cys Leu Arg Pro Met Leu Ala Pro Thr Leu Tyr Asn Tyr Leu Arg
                115                 120                 125

Lys Leu Asp Arg Ile Leu Pro Gly Pro Ile Lys Val Phe Glu Val Gly
            130                 135                 140

Pro Cys Tyr Arg Lys Glu Ser Asp Gly Lys Glu His Leu Glu Glu Phe
```

```
            145                 150                 155                 160
Thr Met Val Asn Phe Cys Gln Met Gly Ser Gly Cys Thr Arg Glu Asn
                165                 170                 175

Leu Glu Ala Leu Ile Lys Glu Phe Leu Asp Tyr Leu Glu Ile Asp Phe
            180                 185                 190

Glu Ile Val Gly Asp Ser Cys Met Val Tyr Gly Asp Thr Leu Asp Ile
        195                 200                 205

Met His Gly Asp Leu Glu Leu Ser Ser Ala Val Val Gly Pro Val Ser
    210                 215                 220

Leu Asp Arg Glu Trp Gly Ile Asp Lys Pro Trp Ile Gly Ala Gly Phe
225                 230                 235                 240

Gly Leu Glu Arg Leu Leu Lys Val Met His Gly Phe Lys Asn Ile Lys
                245                 250                 255

Arg Ala Ser Arg Ser Glu Ser Tyr Tyr Asn Gly Ile Ser Thr Asn Leu
            260                 265                 270

<210> SEQ ID NO 11
<211> LENGTH: 270
<212> TYPE: PRT
<213> ORGANISM: Methanosarcina acetivoran

<400> SEQUENCE: 11

Thr Ser Ala Pro Ala Leu Thr Lys Gly Gln Leu Asp Arg Leu Glu Gly
1               5                   10                  15

Leu Leu Ser Pro Lys Asp Glu Ile Ser Leu Asp Ser Glu Lys Pro Phe
            20                  25                  30

Arg Glu Leu Glu Ser Glu Leu Leu Ser Arg Arg Lys Lys Asp Leu Lys
        35                  40                  45

Arg Ile Tyr Ala Glu Glu Arg Glu Asn Tyr Leu Gly Lys Leu Glu Arg
50                  55                  60

Glu Ile Thr Lys Phe Phe Val Asp Arg Gly Phe Leu Glu Ile Lys Ser
65                  70                  75                  80

Pro Ile Leu Ile Pro Ala Glu Tyr Val Glu Arg Met Gly Ile Asn Ser
                85                  90                  95

Asp Thr Glu Leu Ser Lys Gln Val Phe Arg Ile Asp Lys Asn Phe Cys
            100                 105                 110

Leu Arg Pro Met Leu Ala Pro Asn Leu Tyr Asn Tyr Leu Arg Lys Leu
        115                 120                 125

Asp Arg Ala Leu Pro Asp Pro Ile Lys Ile Phe Glu Ile Gly Pro Cys
130                 135                 140

Tyr Arg Lys Glu Ser Asp Gly Lys Glu His Leu Glu Glu Phe Thr Met
145                 150                 155                 160

Leu Asn Phe Cys Gln Met Gly Ser Gly Cys Thr Arg Glu Asn Leu Glu
                165                 170                 175

Ala Ile Ile Thr Glu Phe Leu Asn His Leu Gly Ile Asp Phe Glu Ile
            180                 185                 190

Ile Gly Asp Ser Cys Met Val Tyr Gly Asn Thr Leu Asp Val Met His
        195                 200                 205

Asp Asp Leu Glu Leu Ser Ser Ala Val Val Gly Pro Val Pro Leu Asp
    210                 215                 220

Arg Glu Trp Gly Ile Asp Lys Pro Trp Ile Gly Ala Gly Phe Gly Leu
225                 230                 235                 240

Glu Arg Leu Leu Lys Val Met His Gly Phe Lys Asn Ile Lys Arg Ala
                245                 250                 255

Ala Arg Ser Glu Ser Tyr Tyr Asn Gly Ile Ser Thr Asn Leu
```

<210> SEQ ID NO 12
<211> LENGTH: 272
<212> TYPE: PRT
<213> ORGANISM: Methanosarcina thermophila

<400> SEQUENCE: 12

```
Thr Ser Thr Pro Ala Pro Ala Leu Thr Arg Ser Gln Leu Asp Arg Ile
1               5                   10                  15

Glu Ala Leu Leu Ser Pro Glu Asp Lys Ile Ser Leu Asp Ala Ala Lys
            20                  25                  30

Pro Phe Arg Glu Leu Glu Ser Glu Leu Leu Glu Arg Lys Gly Asp
        35                  40                  45

Leu Gln Arg Ile Tyr Ala Tyr Glu Arg Glu Asn Tyr Leu Gly Lys Leu
    50                  55                  60

Glu Arg Asp Ile Thr Lys Phe Phe Val Asp Arg Gly Phe Leu Glu Ile
65                  70                  75                  80

Lys Ser Pro Ile Leu Ile Pro Ala Glu Tyr Val Glu Arg Met Gly Ile
                85                  90                  95

Asp Ser Asp Ser Glu Leu Ser Lys Gln Val Phe Arg Val Asp Lys Asn
            100                 105                 110

Leu Cys Leu Arg Pro Met Leu Ala Pro Asn Leu Tyr Asn Tyr Leu Arg
        115                 120                 125

Lys Leu Asp Arg Val Leu Pro Asp Pro Ile Lys Ile Phe Glu Ile Gly
    130                 135                 140

Pro Cys Tyr Arg Lys Glu Ser Asp Gly Lys Glu His Leu Glu Glu Phe
145                 150                 155                 160

Thr Met Leu Asn Phe Cys Gln Met Gly Ser Gly Ser Thr Arg Glu Asn
                165                 170                 175

Leu Glu Ala Leu Ile Arg Glu Phe Leu Asp Tyr Leu Gly Ile Asp Phe
            180                 185                 190

Glu Ile Val Gly Asp Ser Cys Met Val Tyr Gly Asp Thr Leu Asp Val
        195                 200                 205

Met Tyr Gly Asp Leu Glu Leu Ser Ser Ala Val Val Gly Pro Val Pro
    210                 215                 220

Leu Asp Arg Glu Trp Gly Ile Asp Lys Pro Trp Ile Gly Ala Gly Phe
225                 230                 235                 240

Gly Leu Glu Arg Leu Leu Lys Val Met His Gly Phe Lys Asn Ile Lys
                245                 250                 255

Arg Ala Ala Arg Ser Glu Ser Tyr Tyr Asn Gly Ile Ser Thr Ser Leu
            260                 265                 270
```

<210> SEQ ID NO 13
<211> LENGTH: 276
<212> TYPE: PRT
<213> ORGANISM: Desulfitobacterium hafniense

<400> SEQUENCE: 13

```
Phe Trp Thr Lys Val Gln Tyr Gln Arg Leu Lys Glu Leu Asn Ala Ser
1               5                   10                  15

Gly Glu Gln Leu Glu Met Gly Phe Ser Asp Ala Leu Ser Arg Asp Arg
            20                  25                  30

Ala Phe Gln Gly Ile Glu His Gln Leu Met Ser Gln Gly Lys Arg His
        35                  40                  45

Leu Glu Gln Leu Arg Thr Val Lys His Arg Pro Ala Leu Leu Glu Leu
    50                  55                  60
```

```
Glu Gly Lys Leu Ala Lys Ala Leu His Gln Gln Gly Phe Val Gln Val
 65                  70                  75                  80

Val Thr Pro Thr Ile Ile Thr Lys Ser Ala Leu Ala Lys Met Thr Ile
                 85                  90                  95

Gly Glu Asp His Pro Leu Phe Ser Gln Val Phe Trp Leu Asp Gly Lys
            100                 105                 110

Lys Cys Leu Arg Pro Met Leu Ala Pro Asn Leu Tyr Thr Leu Trp Arg
        115                 120                 125

Glu Leu Glu Arg Leu Trp Asp Lys Pro Ile Arg Ile Phe Glu Ile Gly
    130                 135                 140

Thr Cys Tyr Arg Lys Glu Ser Gln Gly Ala Gln His Leu Asn Glu Phe
145                 150                 155                 160

Thr Met Leu Asn Leu Thr Glu Leu Gly Thr Pro Leu Glu Glu Arg His
                165                 170                 175

Gln Arg Leu Glu Asp Met Ala Arg Trp Val Leu Glu Ala Ala Gly Ile
            180                 185                 190

Arg Glu Phe Glu Leu Val Thr Glu Ser Ser Val Val Tyr Gly Asp Thr
        195                 200                 205

Val Asp Val Met Lys Gly Asp Leu Glu Leu Ala Ser Gly Ala Met Gly
    210                 215                 220

Pro His Phe Leu Asp Glu Lys Trp Glu Ile Phe Asp Pro Trp Val Gly
225                 230                 235                 240

Leu Gly Phe Gly Leu Glu Arg Leu Leu Met Ile Arg Glu Gly Thr Gln
                245                 250                 255

His Val Gln Ser Met Ala Arg Ser Leu Ser Tyr Leu Asp Gly Val Arg
            260                 265                 270

Leu Asn Ile Asn
        275

<210> SEQ ID NO 14
<211> LENGTH: 320
<212> TYPE: PRT
<213> ORGANISM: E. coli

<400> SEQUENCE: 14

Val Arg Ser Lys Ile Leu Ala Ala Ile Arg Gln Phe Met Val Ala Arg
1               5                  10                  15

Gly Phe Met Glu Val Glu Thr Pro Met Met Gln Val Ile Pro Gly Gly
                20                  25                  30

Ala Ser Ala Arg Pro Phe Ile Thr His His Asn Ala Leu Asp Leu Asp
            35                  40                  45

Met Tyr Leu Arg Ile Ala Pro Glu Leu Tyr Leu Lys Arg Leu Val Val
    50                  55                  60

Gly Gly Phe Glu Arg Val Phe Glu Ile Asn Arg Asn Phe Arg Asn Glu
65                  70                  75                  80

Gly Ile Ser Val Arg His Asn Pro Glu Phe Thr Met Met Glu Leu Tyr
                85                  90                  95

Met Ala Tyr Ala Asp Tyr His Asp Leu Ile Glu Leu Thr Glu Ser Leu
            100                 105                 110

Phe Arg Thr Leu Ala Gln Glu Val Leu Gly Thr Thr Lys Val Thr Tyr
        115                 120                 125

Gly Glu His Val Phe Asp Phe Gly Lys Pro Phe Glu Lys Leu Thr Met
    130                 135                 140

Arg Glu Ala Ile Lys Lys Tyr Arg Pro Glu Thr Asp Met Ala Asp Leu
145                 150                 155                 160
```

-continued

```
Asp Asn Phe Asp Ala Ala Lys Ala Leu Ala Glu Ser Ile Gly Ile Thr
                165                 170                 175

Val Glu Lys Ser Trp Gly Leu Gly Arg Ile Val Thr Glu Ile Phe Asp
            180                 185                 190

Glu Val Ala Glu Ala His Leu Ile Gln Pro Thr Phe Ile Thr Glu Tyr
        195                 200                 205

Pro Ala Glu Val Ser Pro Leu Ala Arg Arg Asn Asp Val Asn Pro Glu
    210                 215                 220

Ile Thr Asp Arg Phe Glu Phe Phe Ile Gly Gly Arg Glu Ile Gly Asn
225                 230                 235                 240

Gly Phe Ser Glu Leu Asn Asp Ala Glu Gln Ala Glu Arg Phe Gln
                245                 250                 255

Glu Gln Val Asn Ala Lys Ala Ala Gly Asp Asp Glu Ala Met Phe Tyr
                260                 265                 270

Asp Glu Asp Tyr Val Thr Ala Leu Glu Tyr Gly Leu Pro Pro Thr Ala
            275                 280                 285

Gly Leu Gly Ile Gly Ile Asp Arg Met Ile Met Leu Phe Thr Asn Ser
        290                 295                 300

His Thr Ile Arg Asp Val Ile Leu Phe Pro Ala Met Arg Pro Gln Lys
305                 310                 315                 320

<210> SEQ ID NO 15
<211> LENGTH: 321
<212> TYPE: PRT
<213> ORGANISM: Methanosarcina mazei

<400> SEQUENCE: 15

Val Met Arg Ser Lys Leu Ile Ser Glu Ile Arg Arg Tyr Leu Ser Asp
1               5                   10                  15

Arg Glu Phe Leu Glu Phe Glu Thr Pro Ile Leu His Asn Val Tyr Gly
            20                  25                  30

Gly Ala Asn Ala Arg Pro Phe Thr Thr Phe His Asn Cys Leu Gly Gln
        35                  40                  45

Asn Ser Ser Leu Arg Ile Ala Pro Glu Leu Tyr Leu Lys Arg Leu Val
    50                  55                  60

Val Gly Gly Tyr Glu Lys Val Phe Glu Ile Thr Lys Asn Phe Arg Asn
65                  70                  75                  80

Glu Asp Ile Asp Thr Thr His Asn Pro Glu Phe Thr Ile Glu Val
                85                  90                  95

Tyr Glu Ala Tyr Arg Asp Tyr Asn Asp Met Met Asp Leu Thr Glu Gly
            100                 105                 110

Leu Ile Ser Glu Leu Met Phe Lys Leu Thr Gly Ser Tyr Glu Val Lys
        115                 120                 125

Ile Gly Glu Asn Thr Leu Asn Leu Ser Thr Pro Trp Lys Arg Ile Ser
    130                 135                 140

Met Glu Asp Ala Leu Lys Glu Tyr Ala Gly Leu Asp Val Phe Ala His
145                 150                 155                 160

Ser Leu Glu Glu Leu Lys Gln Ile Ala Ile Glu Asn Lys Ile Glu Asp
                165                 170                 175

Tyr Glu Lys Ala Asn Thr Tyr Gly Glu Phe Leu Ala Leu Leu Phe Glu
            180                 185                 190

Gly Leu Val Glu Asp Lys Leu Ile Asn Pro Thr Phe Ile Tyr Asp Tyr
        195                 200                 205

Pro Val Glu Asn Ser Pro Leu Ala Lys Asn Pro Thr Gly Gln Lys Lys
    210                 215                 220
```

-continued

```
Gly Leu Leu Arg Asp Ser Ser Tyr Phe Met Asn Gly Trp Glu Leu Ala
225                 230                 235                 240

Asn Gly Tyr Ser Glu Leu Asn Asp Pro Ile Glu Gln Lys Lys Arg Phe
            245                 250                 255

Glu Glu Gln Asp Lys Lys Arg Lys Leu Gly Asp Leu Glu Ala Gln Thr
        260                 265                 270

Ile Asp Tyr Asp Phe Val Asn Ala Leu Gly Tyr Gly Met Pro Pro Thr
            275                 280                 285

Gly Gly Met Gly Leu Gly Ile Asp Arg Leu Thr Met Ile Leu Val Gly
        290                 295                 300

Leu Asp Ser Ile Lys Glu Val Ile Leu Phe Pro Gln Met Lys Arg Glu
305                 310                 315                 320

Asp

<210> SEQ ID NO 16
<211> LENGTH: 352
<212> TYPE: PRT
<213> ORGANISM: Homo sapiens

<400> SEQUENCE: 16

Ile Arg Ser Lys Ile Ile Thr Tyr Ile Arg Ser Phe Leu Asp Glu Leu
1               5                   10                  15

Gly Phe Leu Glu Ile Glu Thr Pro Met Met Asn Ile Ile Pro Gly Gly
            20                  25                  30

Ala Val Ala Lys Pro Phe Ile Thr Tyr His Asn Glu Leu Asp Met Asn
        35                  40                  45

Leu Tyr Met Arg Ile Ala Pro Glu Leu Tyr His Lys Met Leu Val Val
50                  55                  60

Gly Gly Ile Asp Arg Val Tyr Glu Ile Gly Arg Gln Phe Arg Asn Glu
65                  70                  75                  80

Gly Ile Asp Leu Thr His Asn Pro Glu Phe Thr Thr Cys Glu Phe Tyr
                85                  90                  95

Met Ala Tyr Ala Asp Tyr His Asp Leu Met Glu Ile Thr Glu Lys Met
            100                 105                 110

Val Ser Gly Met Val Lys His Ile Thr Gly Ser Tyr Lys Val Thr Tyr
        115                 120                 125

His Pro Asp Gly Pro Glu Gly Gln Ala Tyr Asp Val Asp Phe Thr Pro
    130                 135                 140

Pro Phe Arg Arg Ile Asn Met Val Glu Glu Leu Glu Lys Ala Leu Gly
145                 150                 155                 160

Met Lys Leu Pro Glu Thr Asn Leu Phe Glu Thr Glu Thr Arg Lys
                165                 170                 175

Ile Leu Asp Asp Ile Cys Val Ala Lys Ala Val Glu Cys Pro Pro Pro
            180                 185                 190

Arg Thr Thr Ala Arg Leu Leu Asp Lys Leu Val Gly Glu Phe Leu Glu
        195                 200                 205

Val Thr Cys Ile Asn Pro Thr Phe Ile Cys Asp His Pro Gln Ile Met
    210                 215                 220

Ser Pro Leu Ala Lys Trp His Arg Ser Lys Glu Gly Leu Thr Glu Arg
225                 230                 235                 240

Phe Glu Leu Phe Val Met Lys Lys Glu Ile Cys Asn Ala Tyr Thr Glu
                245                 250                 255

Leu Asn Asp Pro Met Arg Gln Arg Gln Leu Phe Glu Glu Gln Ala Lys
            260                 265                 270
```

```
Ala Lys Ala Ala Gly Asp Asp Glu Ala Met Phe Ile Asp Glu Asn Phe
        275                 280                 285

Cys Thr Ala Leu Glu Tyr Gly Leu Pro Pro Thr Ala Gly Trp Gly Met
        290                 295                 300

Gly Ile Asp Arg Val Ala Met Phe Leu Thr Asp Ser Asn Asn Ile Lys
305                 310                 315                 320

Glu Val Leu Leu Phe Pro Ala Met Lys Pro Glu Asp Lys Lys Glu Asn
                325                 330                 335

Val Ala Thr Thr Asp Thr Leu Glu Ser Thr Thr Val Gly Thr Ser Val
            340                 345                 350

<210> SEQ ID NO 17
<211> LENGTH: 11
<212> TYPE: PRT
<213> ORGANISM: Unknown
<220> FEATURE:
<223> OTHER INFORMATION: Wild-type tryptic peptide

<400> SEQUENCE: 17

Asn Ser Tyr Ser Pro Ile Leu Gly Tyr Trp Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide resulting from trypsin
      digestion
<220> FEATURE:
<221> NAME/KEY: misc_feature
<222> LOCATION: (3)..(3)
<223> OTHER INFORMATION: Xaa represents Boc-Lys, Aloc-Lys or Z-Lys

<400> SEQUENCE: 18

Asn Ser Xaa Ser Pro Ile Gly Tyr Trp Lys
1               5                   10
```